United States Patent
Lockley et al.

(10) Patent No.: US 12,214,141 B2
(45) Date of Patent: Feb. 4, 2025

(54) METHOD TO SHIFT CIRCADIAN RHYTHM RESPONSIVE TO FUTURE THERAPY

(71) Applicant: Timeshifter, Inc., Southampton, NY (US)

(72) Inventors: Steven Lockley, Somerville, MA (US); Tony Hanna, Copenhagen (DK); Jacob Ravn, Hammenhoeg (SE); Mickey Beyer-Clausen, Southampton, NY (US); Fredric Maxik, Cocoa Beach, FL (US)

(73) Assignee: Timeshifter, Inc., Southampton, NY (US)

( * ) Notice: Subject to any disclaimer, the term of this patent is extended or adjusted under 35 U.S.C. 154(b) by 1001 days.

(21) Appl. No.: 17/248,911

(22) Filed: Feb. 12, 2021

(65) Prior Publication Data

US 2021/0162164 A1    Jun. 3, 2021

Related U.S. Application Data

(63) Continuation-in-part of application No. 16/949,843, filed on Nov. 17, 2020, now abandoned, and a continuation-in-part of application No. 16/432,544, filed on Jun. 5, 2019.

(60) Provisional application No. 62/680,887, filed on Jun. 5, 2018.

(51) Int. Cl.
| | |
|---|---|
| *A61M 21/02* | (2006.01) |
| *A61M 21/00* | (2006.01) |
| *G16H 20/60* | (2018.01) |
| *G16H 20/70* | (2018.01) |

(52) U.S. Cl.
CPC .......... *A61M 21/02* (2013.01); *G16H 20/60* (2018.01); *G16H 20/70* (2018.01); *A61M 2021/0044* (2013.01); *A61M 2205/587* (2013.01)

(58) Field of Classification Search
CPC ... A61B 5/4848; A61B 5/4812; A61B 5/4836; A61B 5/742; A61B 5/0059; A61B 5/7405; A61B 5/0022
See application file for complete search history.

(56) References Cited

U.S. PATENT DOCUMENTS

| | | | |
|---|---|---|---|
| 5,006,985 A | | 4/1991 | Ehret et al. |
| 9,220,202 B2 * | | 12/2015 | Maxik .................. H05B 47/16 |
| 9,827,439 B2 * | | 11/2017 | Maxik .................. H05B 45/20 |

(Continued)

OTHER PUBLICATIONS

United States Patent and Trademark Office, U.S. Appl. No. 16/432,544, Final Office action, mailed on Jan. 13, 2022.

(Continued)

*Primary Examiner* — Michael Collins
(74) *Attorney, Agent, or Firm* — Daniel C. Pierron; Widerman Malek, PL

(57) ABSTRACT

A circadian rhythm shifting method to improve future therapy effectiveness including receiving a future therapy indication, identifying a circadian cycle period that performance of the therapy is preferred, receiving a user normal circadian rhythm indication, defining a user circadian performance time range, identifying a circadian shift to change the user circadian performance time range, defining a user circadian shift protocol to cause the identified circadian shift, and providing an indication to perform an activity of the user circadian shift protocol.

19 Claims, 29 Drawing Sheets

(56) References Cited

U.S. PATENT DOCUMENTS

| | | | |
|---|---|---|---|
| 9,974,973 B2* | 5/2018 | Maxik | H05B 47/19 |
| 10,258,808 B2* | 4/2019 | Maxik | A61N 5/0618 |
| 10,765,886 B2* | 9/2020 | Maxik | H05B 47/19 |
| 2005/0015122 A1 | 1/2005 | Mott | |
| 2006/0106437 A1 | 5/2006 | Czeisler | |
| 2007/0282159 A1 | 12/2007 | Sato | |
| 2010/0100004 A1* | 4/2010 | van Someren | G16H 50/30 |
| | | | 600/595 |
| 2012/0233563 A1 | 9/2012 | Chakra | |
| 2012/0296400 A1 | 11/2012 | Bierman | |
| 2012/0303099 A1 | 11/2012 | D'Ambrosio | |
| 2013/0278172 A1* | 10/2013 | Maxik | G06T 11/001 |
| | | | 315/294 |
| 2014/0067021 A1* | 3/2014 | Rezai | A61N 1/36078 |
| | | | 607/115 |
| 2014/0244332 A1 | 8/2014 | Mermelstein | |
| 2015/0148871 A1 | 5/2015 | Maxik | |
| 2015/0174361 A1 | 6/2015 | Baaijens | |
| 2016/0000380 A1* | 1/2016 | Averina | A61B 5/7275 |
| | | | 600/595 |
| 2016/0270656 A1* | 9/2016 | Samec | A61B 5/14532 |
| 2017/0025028 A1* | 1/2017 | Hrushesky | G09B 19/0076 |
| 2017/0189641 A1 | 7/2017 | Moturu et al. | |
| 2018/0339127 A1 | 11/2018 | Van Reen | |
| 2019/0209806 A1 | 7/2019 | Allen et al. | |
| 2019/0350066 A1 | 11/2019 | Herf et al. | |
| 2020/0129777 A1 | 4/2020 | Muntermann et al. | |
| 2021/0007658 A1 | 1/2021 | Kinnunen et al. | |
| 2021/0093828 A1* | 4/2021 | Fernandes | A61B 5/4839 |
| 2021/0128942 A1* | 5/2021 | Pederson | A61B 5/4848 |
| 2021/0169417 A1* | 6/2021 | Burton | A61B 5/4857 |
| 2022/0037000 A1* | 2/2022 | Shimura | G16H 50/30 |

OTHER PUBLICATIONS

Office Action received on Apr. 26, 2023 in related U.S. Appl. No. 16/949,843.

Office Action received on May 25, 2023 in related U.S. Appl. No. 16/432,544.

United States Patent and Trademark Office, U.S. Appl. No. 16/432,544, Non-Final Office action mailed Oct. 21, 2021.

* cited by examiner

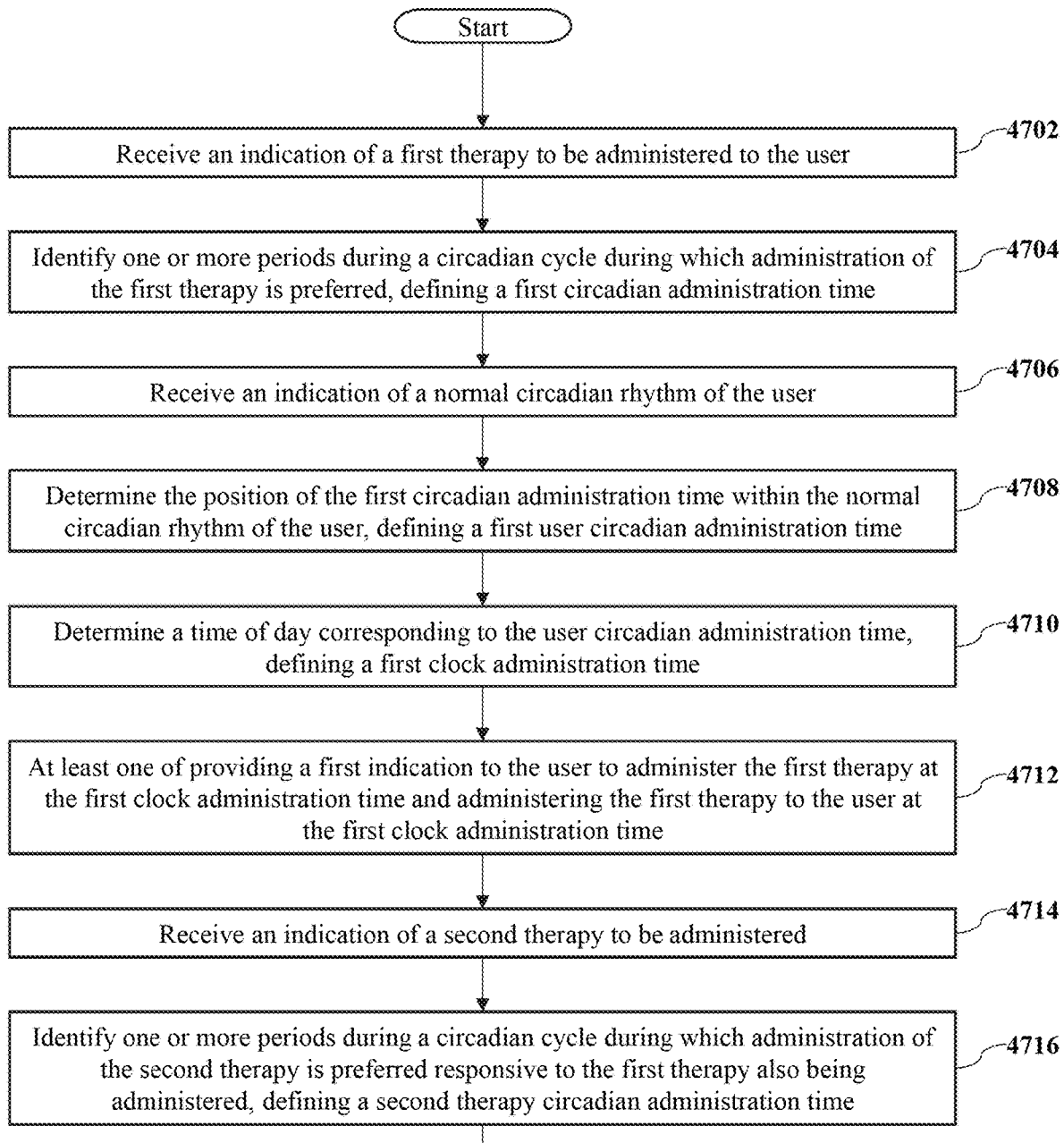

METHOD TO SHIFT CIRCADIAN RHYTHM RESPONSIVE TO FUTURE THERAPY

RELATED APPLICATIONS

This application is a continuation-in-part application of and claims priority under 35 U.S.C. § 120 of U.S. patent application Ser. No. 16/432,544 filed on Jun. 5, 2019 and titled Method and System for Generating and Providing Notifications for a Circadian Shift Protocol, which in turn claims priority under 35 U.S.C. § 119(e) of U.S. Provisional Patent Application Ser. No. filed on Jun. 5, 2018 and titled METHOD AND SYSTEM FOR GENERATING AND PROVIDING NOTIFICATIONS FOR A CIRCADIAN SHIFT PROTOCOL. This application also is a continuation-in-part application of and claims priority under 35 U.S.C. § 120 of U.S. patent application Ser. No. 16/949,843 filed on Nov. 17, 2020 and titled Method to Time Medication and Other Therapies According to Individual Circadian Time. The contents of these applications are incorporated herein by reference.

FIELD OF THE INVENTION

The present invention relates to systems and methods for determining and facilitating shifting of a circadian rhythm of a user to improve the effectiveness of a future therapy.

BACKGROUND OF THE INVENTION

Challenges of shifting an individual's circadian rhythm are well known in the art. Current solutions to shifting circadian rhythms generate protocols that fail to consider the circadian phase of the individual, do not consider whether what is indicated by the protocol is practical and likely to be adhered to be the individual, and are not adapted to prepare multiple, successive protocols that may conflict with one another, as well as other deficiencies. Accordingly, there is a need in the art for a circadian shifting protocol method and system for generating the same that addresses these deficiencies.

The twenty four-hour central circadian clock, located in the suprachiasmatic nuclei (SCN) in the hypothalamus in the brain, controls the daily timing of multiple brain and body systems including sleep, alertness and performance, metabolism, reproductive rhythms, and immune function, among many others. In addition to this central or 'master' circadian clock in the brain, other parts of the brain and peripheral organs and tissues, such as the lungs, liver, heart, pancreas and kidneys, also generate circadian rhythms and work synchronously with the SCN to control and fine-tune local circadian rhythms, such as twenty-four hour rhythms in cardiac, liver, or lung function.

Given the ubiquity of circadian processes, there is increased interest in how to time the administration of various therapies, such as the administration of medication, vaccines, and other pharmaceutical products, and other therapies such as chemotherapy and surgery, to an individual's internal circadian clock, rather than generic timing according to clock time, or without consideration of circadian time.

There is wide variability between individuals in the circadian phase of central and peripheral clocks that ranges from five hours when individuals are studied under highly controlled conditions, to as much as seven to nine hours in people with sleep disorders (e.g., insomnia) or living under irregular schedules, and up to twelve hours in shift workers or after trans-meridian travel (jetlag). This means that a therapy given at 8 a.m. clock time in two individuals might be as much as twelve hours different in circadian time, the equivalent of taking the drug at 8 p.m. in biological time. Several therapies have been shown to vary in their efficacy and safety depending on the time of day which likely vastly underestimates the potential difference in circadian time. Timing therapies based on individual circadian times has enormous potential to improve drug efficacy, for example, inducing the same benefit but with a lower dose, and safety, for example. reducing potentially harmful side-effects or toxicity.

Applicant has previously developed a method for estimating circadian time in order to time 'chronobiotic' treatments, treatments that vary in their effectiveness or effect of the circadian clock based in the circadian time of administration, to address jetlag, changing work schedules, and performance as reflected in U.S. patent application Ser. No. 16/432,544 titled Method and System for Generating and Providing Notifications for a Circadian Shift Protocol filed Jun. 5, 2019, the content of which is incorporated by reference. The method described therein estimates an individual's circadian time based on sleep patterns and chronotype (whether one is a morning type, evening type or neither) in order to time light, light avoidance or melatonin administration, among other activities, to shift the individual's circadian system more quickly than typical approaches (e.g., taking sleeping pills or stimulants, which do not reset the circadian clock).

While previous solutions are directed to shifting a circadian rhythm and performing therapies to maximize the efficacy thereof based on the patient's circadian rhythm, there is no solution that receives information about a future therapy, identifies an ideal circadian phase for the therapy to be administered, identifies a present circadian phase of the patient, and implements a circadian change protocol to shift the circadian rhythm of the patient to align with the ideal circadian phase for the future therapy.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

With the above in mind, embodiments of the present invention are related to a method of determining and facilitating shifting of a circadian rhythm of a user to improve the effectiveness of a future therapy comprising receiving a future therapy indication, the indication comprising a therapy to be administered, a therapy date defining the day the therapy will be administered, and a therapy time defining a time of day the therapy will be administered. The method further comprises identifying one or more periods during a circadian cycle during which performance of the therapy is preferred, defining a circadian performance time range, receiving an indication of a normal circadian rhythm of the user, determining the position of the circadian performance time range within the normal circadian rhythm of the user, defining a user circadian performance time range, and identifying a circadian shift necessary to change the user circadian performance time range such that the therapy time occurs within the user circadian performance time range, the circadian shift comprising a circadian shift direction and a circadian shift magnitude. The method further comprises defining a user circadian shift protocol responsive to the circadian shift direction, circadian shift magnitude, and a number of days between a present day and the therapy date, the user circadian shift protocol comprising one or more activities scheduled to be performed at a certain date and time and providing an indication to perform an activity of the one or more activities comprised by the user circadian shift protocol.

In some embodiments, the one or more activities may comprise at least one of a light exposure or light avoidance activity, a chronobiotic activity, a nutritional consumption activity, a physical activity, and a rest activity. In some embodiments, providing an indication to perform the activity may comprise at least one of illuminating an indicator light, operating a sound-generating device to provide an audio indication, operating a visual display to display a message, and transmitting a message to be received on a computerized device. In some embodiments, the normal circadian rhythm of the user may be at least one of a central circadian clock of the user and a peripheral circadian clock of the user.

In some embodiments, defining a user circadian shift protocol may comprise determining a time of day corresponding to the user circadian performance time, defining a clock performance time, and providing an indication to perform the activity may comprise providing the indication at the clock performance time. In some further embodiments, the method may further comprise receiving an indication of a present circadian phase of the user; wherein the clock performance time is determined responsive to the present circadian phase of the user. In some further embodiments, the present circadian phase may be a first present circadian phase, and the method may further comprise receiving an indication of when the activity was performed, defining a performance time, determining an estimated circadian phase coinciding with the performance time, and determining an estimated efficacy of the activity responsive to the estimated circadian phase, where the estimated efficacy is less than an ideal efficacy. The method may further comprise determining a second user circadian performance time to perform a second performance of the activity responsive to at least one of the estimated efficacy, the circadian performance time, the user circadian performance time, and a second indication of the present circadian phase of the user, determining a second clock performance time responsive to the second user circadian performance time, and providing an indication to the user to perform the second performance of the activity at the second clock performance time.

In some further embodiments, the indication of the present circadian phase of the user and the normal circadian rhythm of the user may be at least one of a sleep-wake cycle of the user, light-dark exposure, chronotype, sex, age, present time zone, future time zone, present work shift, future work shift, heat rate, heart rate variability, core temperature, skin temperature, and a biological marker. In some embodiments, the method may further comprise receiving an indication of when the activity was performed, defining a performance time, determining an estimated circadian phase coinciding with the performance time, and determining an estimated efficacy of the activity responsive to the estimated circadian phase, where the estimated efficacy is less than an ideal efficacy. The method may further comprise determining a second user circadian activity time to perform a second activity of the therapy responsive to at least one of the estimated efficacy, the circadian performance time, and the user circadian performance time, determining a second clock performance time responsive to the second user circadian activity time responsive to the second user circadian activity time, and at least one of providing an indication to the user to perform the second performance of the activity at the second clock performance time and administering the second performance of the therapy to the user at the second clock performance time.

In further embodiments, the activity may be a first activity, the circadian performance time may be a first therapy circadian performance time, the user circadian performance time may be a first activity user circadian performance time, the clock performance time may be a first activity clock performance time, and the indication provided to the user to perform the activity may be a first indication. The method may further comprise receiving an indication of a second activity to be performed, identifying one or more periods during a circadian cycle during which performance of the second activity is preferred responsive to the first activity also being performed, defining a second activity circadian performance time, determining the position of the second circadian performance time within the normal circadian rhythm of the user, defining a second activity user circadian performance time, determining a time of day corresponding to the second activity user circadian performance time, defining a second activity clock performance time, and providing a second indication to the user to perform the second activity at the second activity clock performance time. The first activity circadian performance time may be determined responsive to the second activity also being performed. In some further embodiments, the method may further comprise receiving an indication of a present circadian phase of the user, where each of the first clock performance time and the second clock performance time may be determined responsive to the present circadian phase of the user.

In some further embodiments, providing the first indication to the user to perform the first activity may comprise at least one of illuminating a first indicator light, operating a sound-generating device to provide a first audio indication, operating a visual display to display a first message, and transmitting a first message to be received on a computerized device, and providing the second indication to the user to perform the second activity comprises at least one of illuminating a second indicator light that is differentiated from the first indicator light, operating a sound-generating device to provide a second audio indication that is differentiated from the first audio indication, operating a visual display to display a second message that is differentiated from the first message, and transmitting a second message that is differentiated from the first message to be received on the computerized device.

In some embodiments, the method may further comprise receiving a sleep pattern for the user, wherein the user circadian shift protocol is defined responsive to the sleep pattern. In some embodiments, the method may further comprise receiving an activity preference indication for the user identifying an activity the user will not perform, defining an excluded activity; wherein defining the user circadian shift protocol comprises defining one or more activities excluding the excluded activity. In some embodiments, the method may further comprise receiving an indication of non-performance of an activity, defining a non-performed activity and adjusting the user circadian shift protocol responsive to the non-performed activity.

Further embodiments of the invention may be directed to a system for determining and facilitating shifting of a circadian rhythm of a user to improve the effectiveness of a future therapy comprising a communication device configured to: receive a future therapy indication comprising a therapy to be administered, a therapy date defining the day the therapy will be administered, and a therapy time defining a time of day the therapy will be administered. The communication device may further be configured to receive an indication of a normal circadian rhythm of the user and transmit a message to be received on a computerized device. The system may further comprise a processor positioned in communication with the network communication device and configured to identify one or more periods during a circadian cycle during which performance of the therapy is preferred, defining a circadian performance time range, define a user circadian shift protocol responsive to the circadian shift direction, circadian shift magnitude, and a number of days between a present day and the therapy date, the user circadian shift protocol comprising one or more activities scheduled to be performed at a certain date and time, and at least one of illuminate an indicator light, operate a sound-generating device to provide an audio indication, and operate a visual display to display a message.

In further embodiments, the processor may further be configured to, in defining a user circadian shift protocol, determine a time of day corresponding to the user circadian performance time, defining a clock performance time, and illuminate the indicator light, operate the sound-generating device to provide an audio indication, and operate the visual display to display a message at the clock performance time. The communication device may further be configured to transmit the message to be received on a computerized device at the clock performance time.

In some embodiments, the communication device may be further configured to receive an indication of a present circadian phase of the user, and the processor may further be configured to determine the clock performance time responsive to the present circadian phase of the user. In some embodiments, where the present circadian phase is a first present circadian phase, the communication device may be further configured to receive an indication of when the activity was performed, defining a performance time, and the processor may be further configured to determine an estimated circadian phase coinciding with the performance time, determine an estimated efficacy of the activity responsive to the estimated circadian phase, where the estimated efficacy is less than an ideal efficacy, determine a second user circadian performance time to perform a second performance of the activity responsive to at least one of the estimated efficacy, the circadian performance time, the user circadian performance time, and a second indication of the present circadian phase of the user, determine a second clock performance time responsive to the second user circadian performance time, and at least one of illuminate an indicator light, operate a sound-generating device to provide an audio indication, and operate a visual display to display a message at the second clock performance time. Additionally, the communication device may be further configured to transmit the message to be received on a computerized device at the second clock performance time.

In some embodiments, the communication device may be further configured to transmit the message to be received on a computerized device by at least one of transmitting the message directly to the computerized device and transmitting the message to the computerized device across a network according to a network protocol.

BRIEF DESCRIPTION OF THE DRAWINGS

Some embodiments of the present invention are illustrated as an example and are not limited by the figures of the accompanying drawings, in which like references may indicate similar elements.

FIGS. 47A-B are flow charts illustrating another method according to an embodiment of the invention.

DETAILED DESCRIPTION OF THE INVENTION

Figure 1:
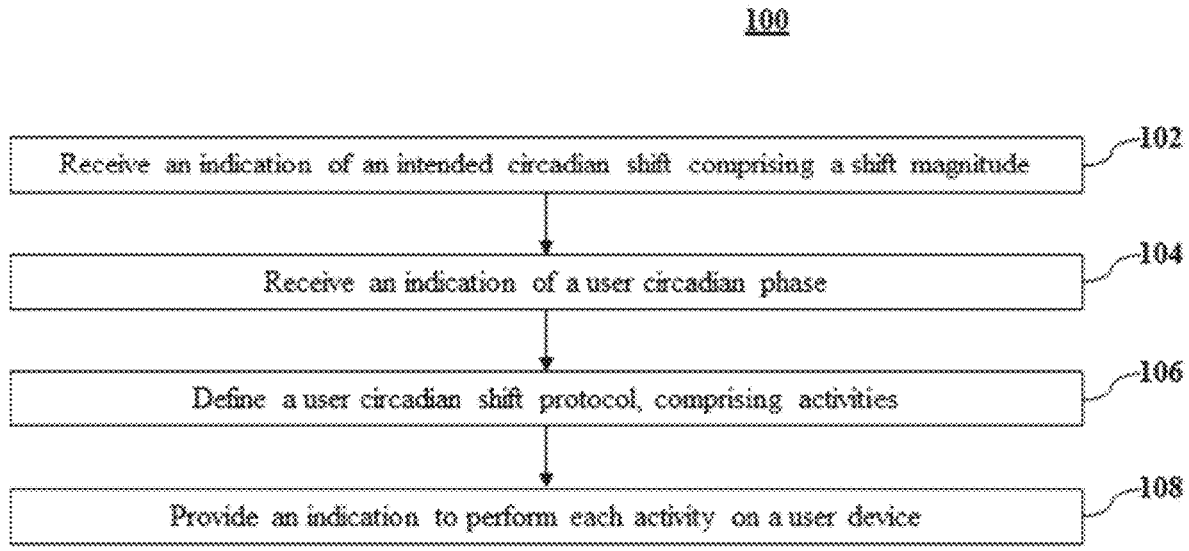
FIG. 1 is a flowchart illustrating a method of generating and displaying a circadian shift protocol according to an embodiment of the invention.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

Referring now to FIGS. 1-14, a computer-implemented method of identifying circadian rhythm change scenarios, determining a circadian rhythm adjustment program responsive to the identified circadian rhythm change scenario, and prescribing at least one intervention designed to effect a change to a circadian rhythm of a circadian rhythm for an individual associated with the identified circadian rhythm change scenario. The method may be implemented on a device comprising a display, a processor operably coupled to the display and operable to control both the display content and the brightness of the display, a memory, and, in some embodiments, a communication device, such as a network communication device, the communication device being operable to communicated using at least one communication protocol, including, but not limited to, wireless communication protocols such as 802.XX protocols, such as Wi-Fi, Bluetooth, Zigbee, Z-Wave, and the like. Additionally, the network communication device may be operable to communicated across at least one of a Personal Area Network (PAN), a Local Area Network (LAN), or a Wide Area Network (WAN), such as the Internet. The communication device may also be operable to communicate with a remote computerized device remotely, i.e. not across a network. The memory may comprise thereon a computer program comprising instructions that are executable by the processor so as to perform the following method. In some embodiments, the device may be a smartphone, comprising a touchscreen display, however it is contemplated and included within the scope of the invention that the method may be performed by any computerized device as described above and operable to receive user input, including input performed using a mouse, a keyboard, a touchscreen, a sensor, and any other user input device as is known in the art. Steps of receiving information may be performed by one of a user input device and the network communication device. Steps of determining, identifying, selecting, creating, adjusting a circadian shift protocol, altering a circadian shift protocol, and modifying a circadian shift protocol is performed by the processor. The steps of displaying and providing an indication may be performed by the processor in conjunction with the display device. Steps of transmitting a command to a computerized device and, in some embodiments, receiving user inputs may be performed by the network communication device. In other embodiments, the method may be implemented on a server that is in communication with a user device via the Internet, such that the following are shown on a display of the user device, user inputs and external circumstances are received by the user device and transmitted to the server, which processes said user input in the generation of the circadian shift protocol. Such a server may further be in communication with the user device to provide notifications according to a determined circadian shift protocol, as will be described in detail below.

Referring now to FIG. 1, a flowchart illustrating a method 100 of determining and presenting a protocol for adjusting a circadian rhythm of a user is presented. The method 100 may comprise receiving an indication of an intended circadian shift for a user, comprising a shift magnitude 102. The circadian shift may be understood as changing the circadian rhythm of the user such that the user's waking/sleeping diurnal pattern is changed to different hours, i.e. the user wakes up at a different time and goes to sleep at a different time. The intended circadian shift represents a target or desired circadian rhythm of the user, taking the form of any target for a circadian rhythm including a target time to wake up, a target time to go to sleep, a target time to be at peak performance, and any other target time for a biological process associated with the circadian rhythm The motivation for such a target circadian rhythm can be varied, including, but not limited to, travelling to a different time zone, desire to rise earlier or later than the user rises at present, going to sleep earlier or later than the user goes to sleep at present, a desire to maximize the body's peak performance, a change in work schedule, and adjustments related to medical conditions, such as insomnia, maximizing drug delivery effectiveness, preparing the body for surgery, and the like. While the portions of the discussion will be constrained to effecting a change in a circadian rhythm as a result of travel, all of the aforementioned motivations and any others as may exist may similarly be presented as options for the user's selection, and follow-up questions pertinent to those objectives may similarly be asked of the user, and input received from the user, to program a circadian rhythm change protocol accordingly.

In some embodiments, the shift magnitude may be expressly provided, i.e. the user indicates a desire to shift their circadian rhythm forward one hour. In some embodiments, the shift magnitude may be understood as a difference between a current, future, or otherwise assumed circadian rhythm of the user and a target circadian rhythm. In some embodiments, the shift magnitude may be determined from information provided by the user, as will be discussed in greater detail herein below.

The indication for the intended circadian shift can take many forms. In some embodiments, the indication can comprise travel information related to a user trip. The travel information may indicate a change in time zone, where the change in time zone at least partially, and in some embodiments fully, defines the shift magnitude. The travel information may comprise a departure date, a departure time, a departure location, an arrival date, an arrival time, and an arrival location. The difference between time zones of the departure location and the arrival location may define the shift magnitude. This type of inferring or determining a shift magnitude is exemplary only and does not limit the scope of the invention. A shift magnitude may be determined or inferred from other information, including, but not limited to, a scheduled event (such as a sporting event, academic evaluation, or meeting, etc.), a prescribed time to take medication, a change in time related to daylight saving time, a change in work schedule (including a change in day/night or first/second/third shift), and the like.

The method may design a protocol responsive to the entered flights, accounting for the duration of stopovers or at any destination, such that, in some instances, a partial circadian shift is affected, such that the user may more expediently shift to a circadian rhythm aligned with the time zone to which they are going, if the magnitude difference in time zones between the travel destination and the return, or onwards, destination is too great for a complete shift to be accomplished, the number of days until departure is too small to affect a complete circadian change so as to adjust the user to a circadian rhythm aligned with the destination time zone, and/or the duration of the trip is so short as to not warrant a complete circadian shift. These motivations, and any others, may each be weighted by the method, in some instances according to user input in terms of user preference, and the circadian shift protocol designed accordingly.

The method 100 may continue with receiving an indication of a user circadian phase 104. The indication of the user circadian phase may take many forms, including, but not limited to, an indication from the user as to what their diurnal preference, or choronotype, is (e.g. early bird, night owl, or neither). Further indications of the user's circadian phase may include physiological measurements. These indications are exemplary only, and any indication of a user circadian phase is contemplated and included within the scope of the invention.

The method 100 may continue with defining a user circadian shift protocol responsive to the shift magnitude and the indication of the user circadian phase. Defining the protocol may comprise scheduling one or more circadian-shifting activities to be performed at a certain date and time, with the totality of the activities defining the protocol. Each of the activities may be designed to affect the intended circadian shift. The types of activities comprised by the protocol may include, but are not limited to, light exposure and/or light avoidance activities, chronobiotic activities, nutritional consumption activities, physical activities, and rest activities. Light exposure/avoidance activities may include, but are not limited to, seeking out exposure to light, seeking out exposure to daylight, seeking out exposure to light comprising light within a blue range of the physical spectrum (i.e. light within a wavelength range from 450 nanometers (nm) to 485 nm), avoiding light, avoiding daylight, and avoiding light comprising light within the blue range, including any timing, duration, pattern, and intensity. Chronobiotic activities may include ingestion of sleep aid, or supplements or chronobiotics (drugs that shift the timing of circadian rhythms(s)) such as melatonin or its agonists (by any method, including melatonin pills, patches, and beverages). Nutritional consumption activities may include ingestion of stimulants such as caffeine (by any method, including drinking caffeinated beverages such as tea or coffee or pills) or other nutritional intake (such as eating meals or snacks). Physical activities may include exercise of any type, and of any duration, intensity, timing, and frequency. Rest activities may include overnight and/or day time sleeping intended to accomplish one or more complete sleep cycles including wake up times and going to sleep times, and napping (i.e. sleep that does not accomplish complete sleep cycles). It is contemplated and included within the scope of the invention that each of these activities may be characterized as "strongly recommended/mandatory," "optional," and other indications of the importance of performing the action. Such indications may be responsive to the effect each activity has on shifting the circadian rhythm of the user, with more effective activities tending to be characterized as "strongly recommended/mandatory" and less effective activities tending to be characterized as "optional."

The method 100 may further comprise providing an indication to perform each activity comprise by the protocol on a user device 106. The indications may comprise a textual reminder to perform the activity, an iconographic reminder to perform the activity, a haptic indication, generating a colored light, an audio indication in the form of a voice reminder, a musical/tonal reminder, or any other sound to indicate the activity to be performed. In some embodiments, the indication may be presented within the context of a calendar, with the portion of the calendar occupied by the indication to perform the activity representing the date and time during which the activity is to be performed. Examples of such indications are shown in FIGS. 34-41, as will be discussed in greater detail below.

In some embodiments, the user may provide an indication as to how they want to receive notifications about the circadian shift protocol resulting from the method. Such notifications may be provided by any means or method known in the industry, including, but not limited to, push notifications, text messages, multimedia messages, e-mails, automated telephone calls, and the like.

In some embodiments, a sleep pattern for the user may also be received, distinct from the indication of the user circadian phase. In such embodiments, the protocol may be defined responsive to the received sleep pattern. In some embodiments, an activity preference may be received from the user. Such activity preferences may include an activity the user does not wish to perform (defining an excluded activity), an activity the user prefers to perform (defining a preferred activity), and time ranges for either of the excluded or preferred activities, indicating if there is just a certain time the user wishes to exclude or promote the respective activities. The protocol may be defined responsive to either or both of the excluded activity and the preferred activity, as well as the respective time ranges.

Resting activities may comprise one or more naps. Information on when and for how long to nap either before, during or after a flight may be provided, either as specific timing or ranges of opportunity during which a shorter nap could be taken. These naps may be further categorized into 'strongly recommended/mandatory' or 'optional' based on prior sleep opportunity, time awake and/or the likelihood that people will need them or can do them.

Napping, both in terms of time and duration, may have certain controls. For example, a nap after landing may be no longer than three hours in length, and must end no later than two hours after a user's typical sleeping end time. A nap before an early flight is limited to three hours in length and can only start a maximum of two hours before a user's typical sleep start time. Moreover, pre-flight naps may be limited to one hour in length.

In addition to the times when sleep is recommended on the airplane, optional naps may also be indicated when there is an extended episode of time without scheduled sleep on the ground, in order to avoid excessive sleep loss. These will be scheduled to occur at times when they will have the least impact on light exposure or the ability to sleep at the destination.

In some embodiments, an indication of non-performance of an activity may be received, defining a non-performed activity. Such an indication may be for an activity that was intended to have already been performed, intended as being presently performed, or intended to be performed in the future. The protocol may be modified to reflect the non-performed activity while still accomplishing the intended circadian shift.

Figure 2:
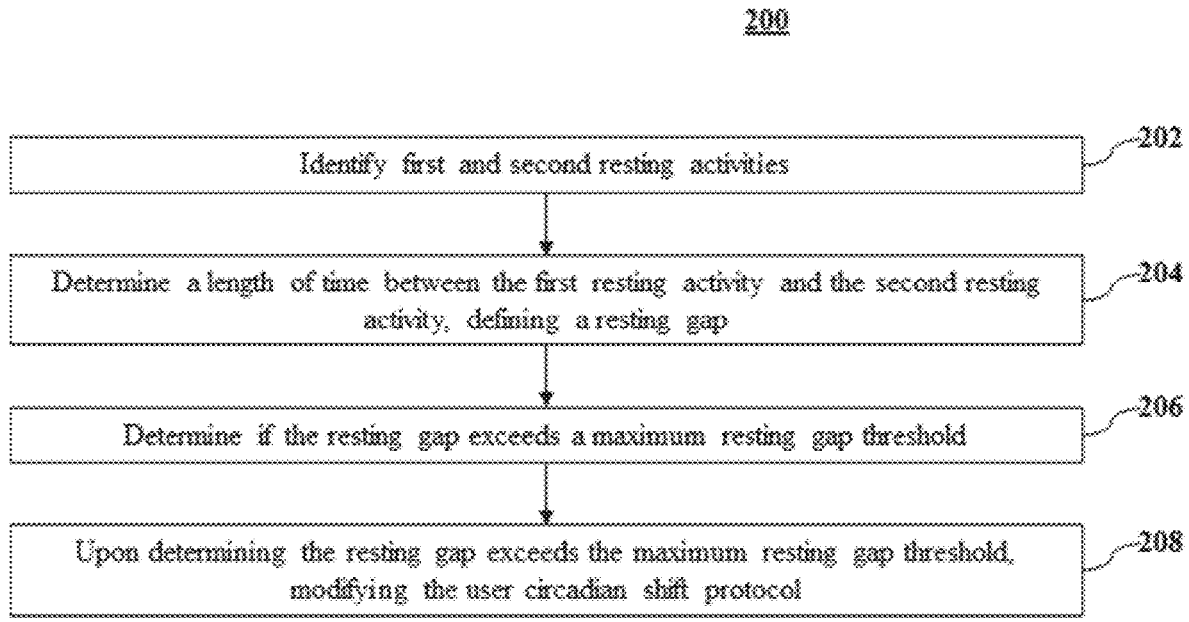
FIG. 2 is a flowchart illustrating a method of ensuring a circadian shift protocol includes adequate resting activities according to an embodiment of the invention.

Referring now to FIG. 2, a method 200 of ensuring a circadian shift protocol includes adequate resting activities according to an embodiment of the invention. The method 200 may comprise identifying a first resting activity and a second resting activity of a user circadian shift protocol. The first and second resting activities may be selected such that there are no other resting activities comprised by the protocol are scheduled between them, i.e. they are succeeding resting activities. The method 200 may continue with determining a length of time between the first and second resting activities, defined as a resting gap 204. This may be measured as a stop time of the first resting activity and a start time of the second resting activity. The method 200 may continue with determining if the resting gap exceeds a resting gap threshold 206. The resting gap threshold may be understood as a maximum amount of time that is preferred not to be exceeded. This may also be understood as a maximum continuous waking duration. The resting gap may be pre-defined, and in some embodiments may be defined responsive to a user indication, such as the user's circadian phase or chronotype, or a maximum amount of time selected by the user. Upon determining the resting gap exceeds the maximum resting gap threshold, the protocol may be modified by at least one of altering at least one of the first resting activity and the second resting activity such that the resting gap is reduced to no longer exceed the maximum resting gap threshold, and creating a new resting activity scheduled between the first resting activity and the second resting activity.

Figure 3:
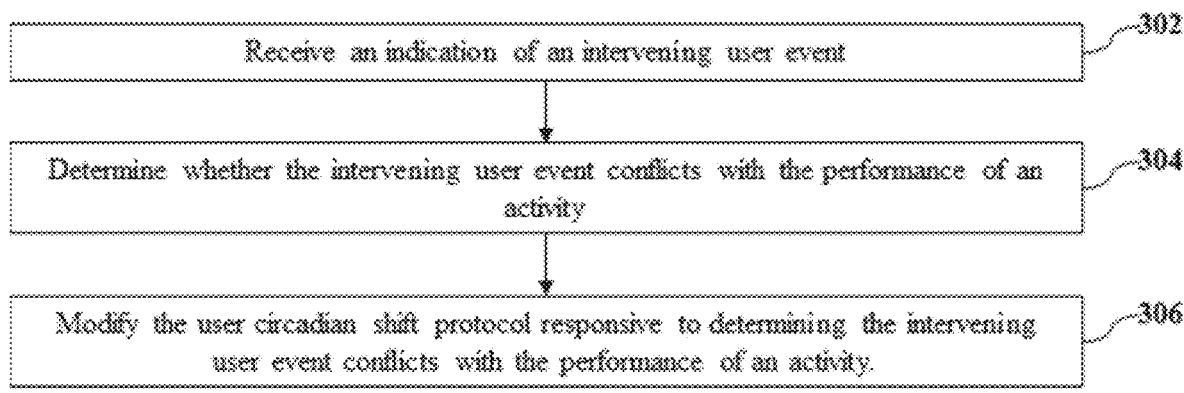
FIG. 3 is a flowchart illustrating a method of modifying a circadian shift protocol responsive to an intervening event according to an embodiment of the invention.

Referring now to FIG. 3, a method 300 of modifying a circadian shift protocol responsive to an intervening event according to an embodiment of the invention is presented. The method 300 may comprise receiving an indication of an intervening user event 302. An intervening user event may be understood as an event related to the user that is not part of the user circadian shift protocol, but is scheduled to occur during the duration of the user circadian shift protocol. The intervening event may be received as an input from the user or other individual, from a calendar (e.g. a calendar provides an indication that an event is occurring at the same time as an activity comprised by the protocol), or any other means or method of receiving an indication of an event. The method 300 may comprise determining whether the intervening user event conflicts with the performance of an activity 304. Such a determination may include first determining if the event coincides with an activity comprised by the protocol, e.g. they are scheduled to occur at the same time. If there is coincidence, the determination may further comprise determining if the nature of the intervening event and the type of activity precludes performance of the activity. For example, if the event is attending a concert and the activity is sleeping, the event precludes performance of the activity. As another example, if the event is to attend a meeting and the activity is to consume caffeine, specifically drink a caffeine-containing beverage, the event does not preclude performance of the activity. If the event precludes performance of the activity, the method 300 may continue with modifying the protocol 306. Such modification may include changing the activity type and/or rescheduling the activity.

Additionally, when determining the circadian shift protocol, certain limitations may be imposed upon when certain activities, exposures, and ingestions occur. For example, users may be required to wake up at least four hours prior to travelling, to permit for adequate transit and check-in time at the airport, which might be in conflict with what a circadian shift would suggest (e.g. sleeping until two hours prior to take-off may be more conducive to obtaining a desired circadian shift). Additionally, as another example, limitations on when a user is unable to comply with certain recommended activities, exposures, and ingestions are contemplated and accounted for. For example, while it might result in a more favorable circadian shift if complied with, an individual may be unable to sleep during a recommended time period, particularly if that individual is boarding a flight or scheduled to travel by car or taxi, for example. Accordingly, the method may take into account such real world or environmental factors, and may generate a circadian shift protocol that eliminates recommendations that are impossible or difficult to comply with, instead making recommendations that have a similar, although moderated, circadian shifting effect. Additionally, as another example, limitations on when a user is likely to comply with certain recommended activities, exposures, and ingestions are contemplated and accounted for. For example, while it might result in a more favorable circadian shift if complied with, an individual may be unlikely to sleep from 4 a.m. to 11 a.m., particularly if that individual has indicated they have a 'morning type' diurnal preference, e.g. early bird. Accordingly, the method may comprise creating a circadian shift protocol that has the user sleep from 2 a.m. to 9 a.m. (or some other time period as may be likely to be complied with by the user) and then avoid sunlight from 9 a.m. to 11 a.m. In this way, the method may generate a circadian shift protocol that minimizes recommendations that are unlikely or very difficult to comply with, instead making recommendations that have a similar, although moderated, circadian shifting effect. Additionally, as another example, limitations on when a user is likely to comply with certain recommended activities, exposures, and ingestions are contemplated and accounted for. For example, while it might result in a more favorable circadian shift if complied with, an individual may be not be able to sleep or nap right upon arrival to a destination as the individual will first need to get their luggage, drive to their hotel, check in, unpack their toothbrush etc. before they can go to sleep.

The circadian shift protocol may be connected to a user's calendar, allowing appointments and tasks to be scheduled at a time optimal for such appointment or task. If more users connect their circadian shift protocol to their calendars, the calendar may recommend the best time to meet, talk, or executive tasks together, based on their circadian shift protocols.

Figure 4:
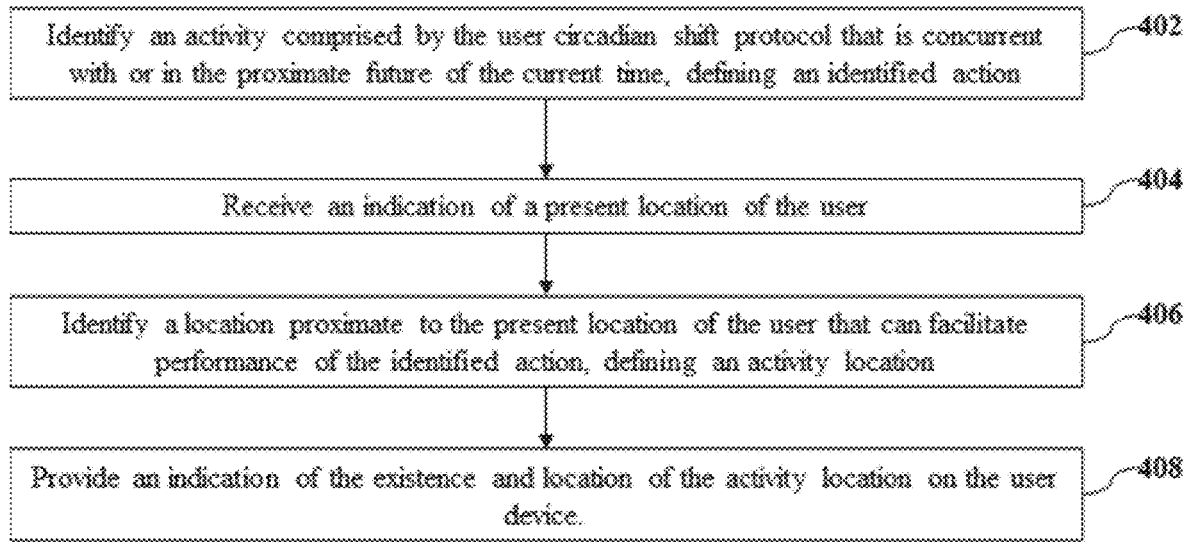
FIG. 4 is a flowchart illustrating a method of facilitating performance of an activity of a circadian shift protocol according to an embodiment of the invention.

Referring now to FIG. 4, a method 400 of facilitating performance of an activity of a circadian shift protocol according to an embodiment of the invention is presented. The method 400 may comprise identifying an activity comprised by the user circadian shift protocol that is concurrent with or in the proximate future of the current time, defining an identified action 402. The method 400 may continue with receiving an indication of a present location of the user 404. Such an indication may be received by any means or method known in the art, including, but not limited to, receiving a location indication from a GPS device, including a GPS device comprised by a user device, a location indication inferred from an IP address or Wi-Fi network IP address, an indication from a map software operated by the user or other individual associated with the user, and the like. The method 400 may continue with identifying a location proximate to the location of the user that can facilitate performance of the identified action, defining an activity location 406. Such activity locations are responsive to the type of activity. For example, if the activity is a physical activity, specifically exercising, the activity location could be a park with a running trail, a fitness center or gymnasium, and the like. As another example, if the activity is to consume a caffeine-containing beverage, the activity location may be a coffee shop, tea shop, or vending machine containing energy drinks. The identification of the activity location may result from querying a service or database that comprises the location and types of goods or services at such locations with the present location of the user and the identified action, as is known in the art. The method 400 may continue with providing an indication of the existence and location of the activity location on the user device 408. Such an indication may include audio, graphical, and/or textual indications of the activity location, where it is located, navigation information, open-close times, and how it is related to the identified action.

Figure 5:
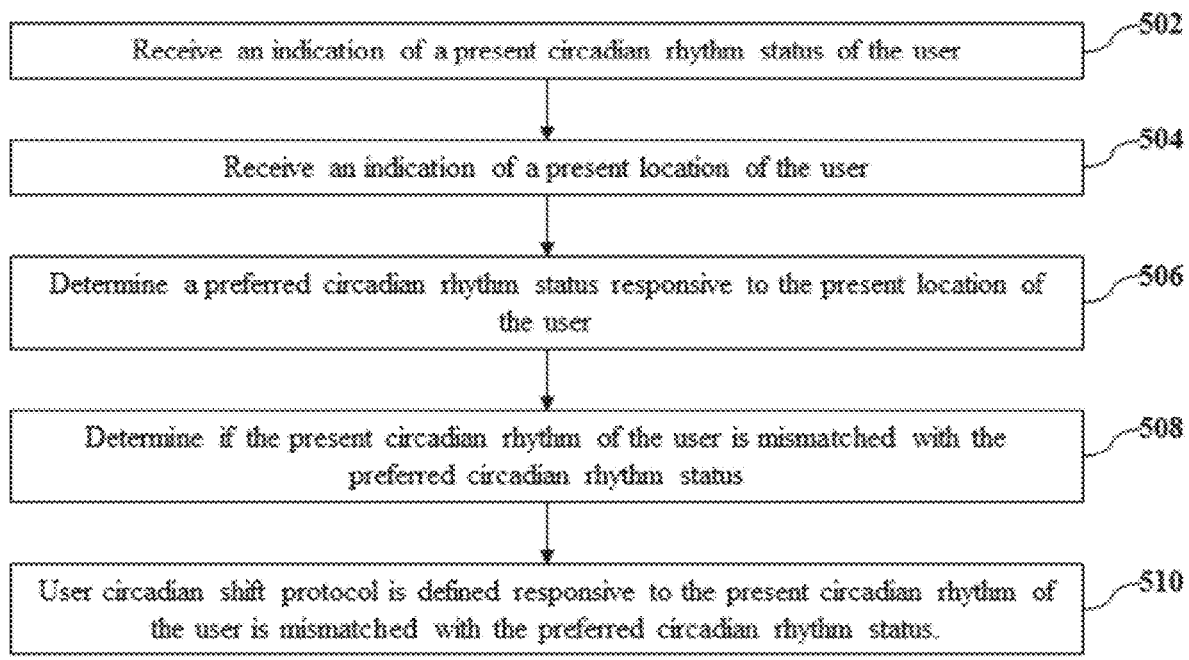
FIG. 5 is a flowchart illustrating a method of defining a circadian shift protocol responsive to a circadian status of the according to an embodiment of the invention.

Referring now to FIG. 5, a method 500 of defining a circadian shift protocol responsive to a circadian status of the according to an embodiment of the invention is presented. The method 500 may comprise receiving an indication of a present circadian rhythm status of the user 502. Such an indication may comprise any information that demonstrates, suggests, or otherwise supports a determination of the circadian rhythm status of the user, including, but not limited to, sleep history information, waking time information, time of day, physiological measurement information, and the like. The method 500 may continue with receiving a present location of the user 504, similar to step 404 of FIG. 4 as described herein above. The method 500 may continue with determining a preferred circadian rhythm status for the user responsive to the present location of the user 506. More specifically, a circadian rhythm may be determined for the user based on the user location, and based on one or both of the time of day and the user's circadian phase/chronotype, the preferred circadian rhythm status may be determined. The method 500 may continue with determining if the present circadian rhythm of the user is mismatched with the preferred circadian rhythm status 508. Such a mismatch may be determined by comparing the user's present circadian rhythm and identifying if they are ahead, behind, or aligned with the preferred circadian rhythm status. If there is a mismatch, the method 500 may continue with defining the user circadian shift protocol responsive to the mismatch 510. Defining the protocol responsive to the present circadian rhythm status of the user increases compliance with and effectiveness of the protocol.

In some embodiments, defining the user circadian shift protocol may comprise determining whether advancing the user's circadian rhythm (e.g. making their rise time and bed time earlier) or delaying their circadian rhythm (e.g. making their rise time and bed time later) is most effective and preferable. Such a determination may be made responsive to at least the shift magnitude, the direction of the shift, and the user circadian phase, including the user chronotype. It may further be determined whether an advancing circadian shift protocol that advances the user's circadian rhythm or a delaying circadian shift protocol that delays the user's circadian rhythm is preferred, defining a preferred shifting direction. Accordingly, the user circadian shift protocol may be defined responsive to the preferred shifting direction.

Figure 6:
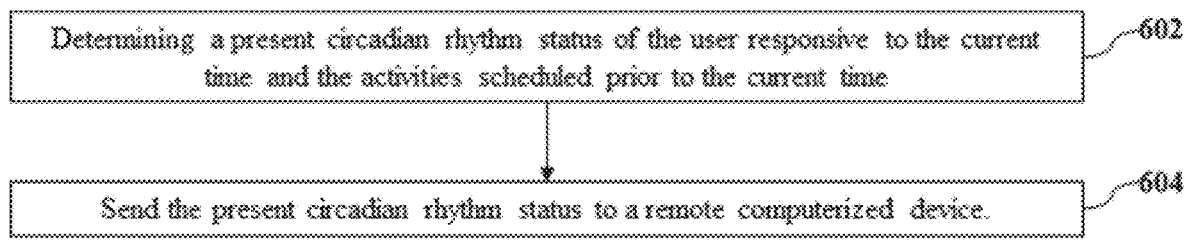
FIG. 6 is a flowchart illustrating a method of providing an indication of a user circadian status according to an embodiment of the invention.

Referring now to FIG. 6, a method 600 of providing an indication of a user circadian status according to an embodiment of the invention is presented. The method 600 may comprise determining a present circadian rhythm status of the user 602. Such a status may be determined responsive to at least the current time and the activities scheduled prior to the current time. This determination may presume the performance of the previously scheduled activities and their attending effect on the circadian rhythm of the user. The method 600 may continue with sending the present circadian rhythm status to a remote computerized device 604. This may be accomplished by transmitting an indication of the status using a network communication device as discussed herein above. Moreover, the remote computerized device may be associated with an entity other than user, such as a hotel operator, a car rental company, a medical professional, or any other entity. The receiving entities make take any action responsive to the status, such as preparing a room responsive to the status, e.g. prepared for an immediate nap or provision of caffeine-containing items, determining whether the user is in an appropriate and safe status to rent and drive a car, and any other action.

Figure 7:
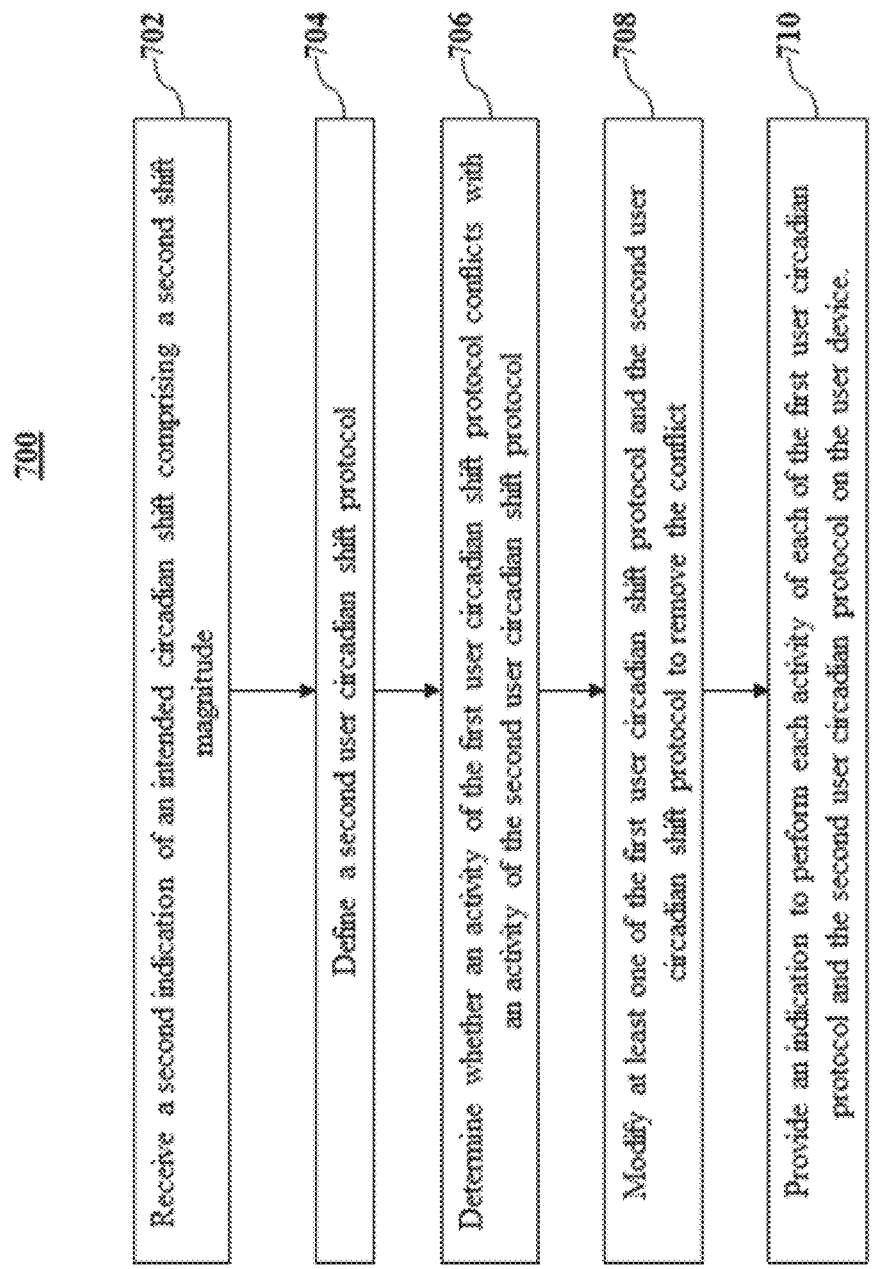
FIG. 7 is a flowchart illustrating a method of generating a second circadian shift protocol and modifying a circadian shift protocol responsive to a shift protocol conflict according to an embodiment of the invention.

Referring now to FIG. 7, a method 700 of generating a second circadian shift protocol and modifying a circadian shift protocol responsive to a shift protocol conflict according to an embodiment of the invention is presented. In this embodiment, the protocol generated in FIG. 1 may be considered a first user circadian shift protocol. The method 700 may comprise receiving a second indication of an intended circadian shift comprising a second shift magnitude 402. The second indication may be in addition to the first indication shown at 102 in FIG. 1. The method 700 may continue with defining a second user circadian shift protocol responsive to the second shift magnitude and the user circadian phaser 704, with the user circadian phase having been received at 104 in FIG. 1. The second user circadian shift protocol may comprise circadian-shifting activities of the types described herein above. The method 700 may continue with determining whether an activity of the first user circadian shift protocol conflicts with an activity of the second user circadian shift protocol. Types of conflicts include whether the activities are coincident and unable to be performed simultaneously and/or the activities of one protocol are scheduled to occur during the performance of the other protocol and shift the circadian rhythm of the user in a manner that is inconsistent or not conducive with producing the intended circadian shift of the other protocol. Upon determining an activity of the first user circadian shift protocol conflicts with an activity of the second user circadian shift protocol, the method 700 may continue with modifying at least one of the first user circadian shift protocol and the second user circadian shift protocol to remove the conflict 708. Such modification may take the form of rescheduling one or both of the conflicting activities, changing the activity type of one or both of the conflicting activities, and combinations thereof. The method 700 may continue with providing an indication to perform each activity of the first and second user circadian shift protocols on the user device 710.

As mentioned above, the intended circadian shift may be related to a user trip, and the indication for the intended shift may be travel information. In such embodiments, the travel information may comprise a departure date, a departure time, a departure location, an arrival date, an arrival time, and an arrival location. FIGS. 8-14 are directed to such embodiments.

Figures 8, 9:
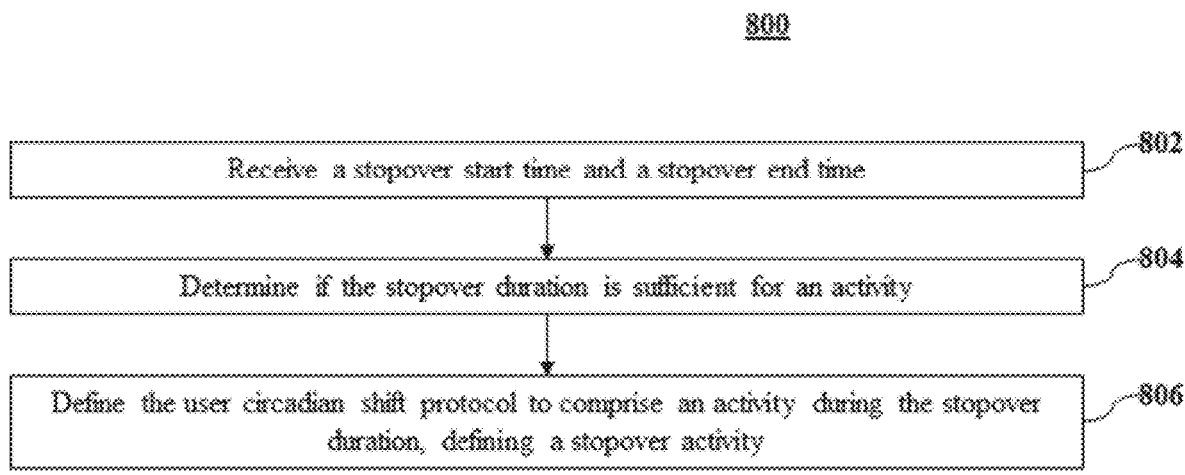
FIG. 8 is a flowchart illustrating a method of defining a circadian shift protocol comprising an activity to be performed during a travel stopover according to an embodiment of the invention.
FIG. 9 is a flowchart illustrating a method of defining a partial circadian shift protocol according to an embodiment of the invention.

Referring now to FIG. 8 a method 800 of defining a circadian shift protocol comprising an activity to be performed during a travel stopover according to an embodiment of the invention is presented. The method 800 may comprise receiving travel information comprising a stopover start time and a stopover end time, with the time between the stopover start time and the stopover end time defining a stopover duration. The method 800 may continue with determining if the stopover duration is sufficient for an activity 804. The type of activity considered may affect this determination. For example, an activity involving napping would require the user having sufficient time to go to an area appropriate for napping, napping, and getting to where the user needs to be by the stopover end time. Another example is an activity involving consuming caffeinated beverage would require time for the user to go to a location that provides such beverages, time to order and consumer the beverage, and time to get to where the user need to be at the stopover end time. Activities included in this determination include, but are not limited to, light exposure or light avoidance activities, chronobiotic activities, nutritional consumption activities, physical activities, and rest activities. The method 800 may further comprise defining the user circadian shift protocol to comprise an activity during the stopover duration, defining a stopover activity.

Referring now to FIG. 9, a method 900 of defining a partial circadian shift protocol according to an embodiment of the invention is presented. The method 900 may comprise determining a pre-arrival time, defined as a length of time between a present time and the arrival time on the arrival date 902. The method 902 may further comprising determining a pre-arrival required daily shift to accomplish a preferred circadian shift to a time zone associated with the arrival location 904. This may be understood as the amount the user's circadian rhythm must shift each day to accomplish the preferred circadian shift by the arrival time. In some embodiments, such a preferred circadian shift may be a complete circadian shift, i.e. the user is fully shifted to a target circadian rhythm associated with the arrival location. In some embodiments, such a complete shift may be impractical, necessitating the user to pre-shift their circadian rhythm to an extent that is not conducive to conducting their life, thereby decreasing the likelihood of compliance with the protocol. In such embodiments, the preferred circadian shift to be accomplished by the arrival time on the arrival date may be only a portion of the complete circadian shift, with the remainder of the complete circadian shift to be accomplished after arrival. It is contemplated and included within the scope of the invention to define a user circadian shift protocol for the target circadian shift to be accomplished prior to the arrival time, at the arrival time, or after the arrival time, with the method determining which is most practical and likely to be adhered to by the user.

The method 900 may further comprise determining whether the prearrival required daily shift exceeds a maximum daily shift. The maximum daily shift may be understood as a maximum amount a user can shift their circadian rhythm each day. This is commonly understood to be between 1-2 hours per day. However, it is contemplated and within the scope of the invention that the protocol may be defined assuming a maximum daily shift of three hours, accounting for the improvement that circadian-shifting activities affects on circadian-shifting capabilities of the user, when compared to non-performance of such circadian-shifting activities. In some embodiments, the user may set or adjust the maximum daily shift.

Upon determining the pre-arrival required daily shift exceeds the maximum daily shift, the method 900 may continue with modifying the user circadian shift protocol to accomplish a partial circadian shift by the arrival time on the arrival date 908. This means that only a portion of the preferred circadian shift will be accomplished at arrival time, regardless of whether the preferred circadian shift is a complete shift or a partial shift.

Figure 10:
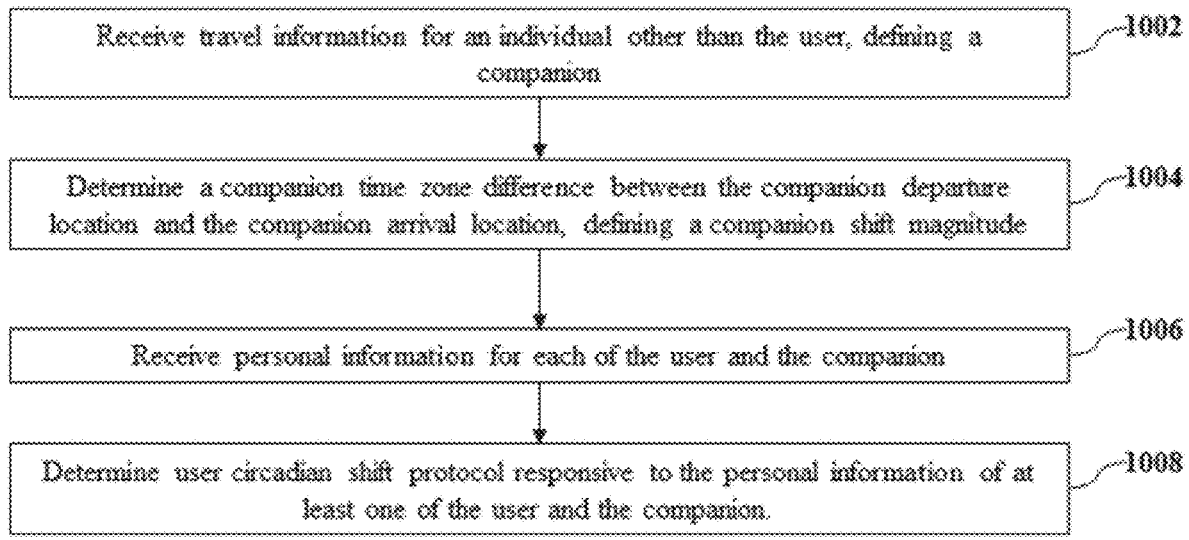
FIG. 10 is a flowchart illustrating a method of defining a circadian shift protocol for a travel companion according to an embodiment of the invention.

Referring now to FIG. 10, a method 1000 of defining a circadian shift protocol for a travel companion according to an embodiment of the invention is presented. The method 1000 may comprise receiving travel information for an individual other than the user, defining a companion 1002. The travel information may comprise information similar to that of the user's travel information, such as a companion departure date, a companion departure time, a companion departure location, a companion arrival date, a companion arrival time, and a companion arrival location. The method 1000 may further comprise determining a companion time zone difference between the companion departure location and the companion arrival location, defining a companion shift magnitude. In some embodiments, any or all of the companion travel information may be the same as the user travel information. In some embodiments, some of the companion travel information may be different from the user travel information. In most embodiments, there will be a connection between the user and the companion, such as a motivation for the intended circadian shift or the same arrival location, such that the user and the companion are on roughly the same circadian rhythm, accounting for their individual differences (e.g. difference in user circadian phase, chronotype, etc.).

The method 1000 may further comprise determining a companion time zone difference between the companion departure location and the companion arrival location, defining a companion shift magnitude 1004, similar to step 106 of FIG. 1. The method 1000 may further comprise receiving personal information for each of the user and the companion 1006. Such personal information may include any information about the user and companion, respectively, that may information performance of step 1008, determining the user circadian shift protocol responsive to the personal information of at least one of the user and the companion. Types of personal information include, but are not limited to, age, medical conditions, personal habits, and any other information that may relate to a greater or lesser need for the user circadian shift protocol to be adjusted to that need. As an example, if the companion is an infant, the protocol would need to reflect the ability to accommodate frequent napping and feeding, precluding long naps for the user. As another example, for a family travelling abroad, a single user may provide inputs for each member of the family that is travelling together. In another example, for a business trip including multiple adults, each adult may input their own information. In some embodiments, after each additional user information is inputted, the method may comprise determining a circadian rhythm responsive to the various inputs received. In some embodiments, some user inputs may be weighted more heavily than others, for example, a child's input may be given more or less weight than an adult's, an elderly person's input may be given more or less weight, a person with a medical requirement may be given more weight, etc. In other embodiments, a user providing an input may indicate that, when they have completed providing their input, no more users inputs will be included in the combination circadian shift protocol.

Figure 11:
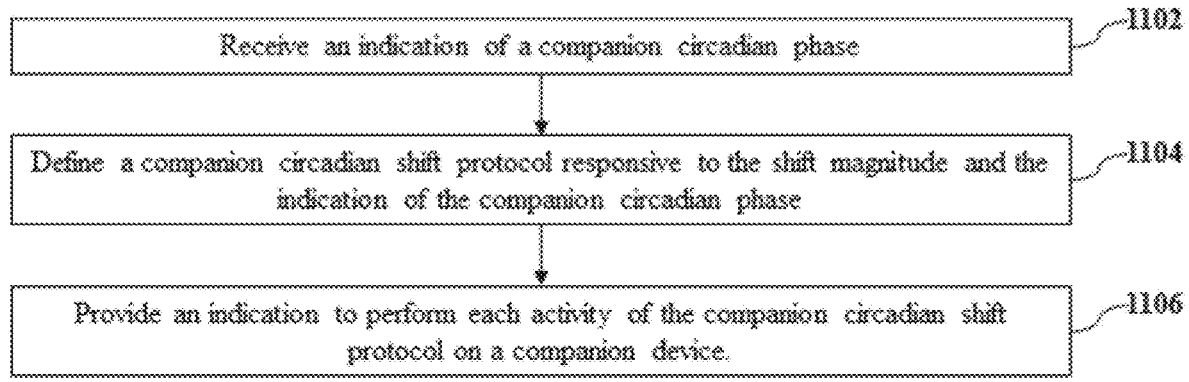
FIG. 11 is a flowchart illustrating a method of defining a circadian shift protocol for two individuals according to an embodiment of the invention.

Referring now to FIG. 11, a method 1100 of defining a circadian shift protocol for two individuals according to an embodiment of the invention is presented. The method 1100 may be contemplated as being performed in conjunction with method 1000 of FIG. 1000. The method 1100 may comprise receiving an indication of a companion circadian phase, similar to the user circadian phase received in step 104 of FIG. 1. The method 1100 may further comprise defining a companion circadian shift protocol responsive to the companion shift magnitude as shown in 1004 of FIG. 10 and the companion circadian phase 1104. The companion circadian shift protocol may comprise circadian-shifting activities as described hereinabove. The method 1100 may further comprise providing an indication to perform each activity of the companion circadian shift protocol on a device, such as a companion smart phone. In some embodiments, the user device may be utilized for providing indications of the companion circadian shift protocol activities. Such embodiment may be useful where the companion requires a different circadian shift protocol than the user. For example, children may be more likely to take naps, but less likely to ingest caffeinated beverages, and therefore may have a first circadian shift protocol having greater reliance on certain activities, exposures, and substance ingestion and less reliance on others. In contrast, adults may be less likely to take naps but more likely to ingest caffeinated beverages, and therefore may have a circadian shift protocol responsive to those tendencies. Elderly adults may be relatively more likely to take naps and ingest caffeinated beverages, and therefore a circadian shift protocol responsive to these tendencies may be configured, differentiated in the recommendations made from those for children or adults.

Figure 12:
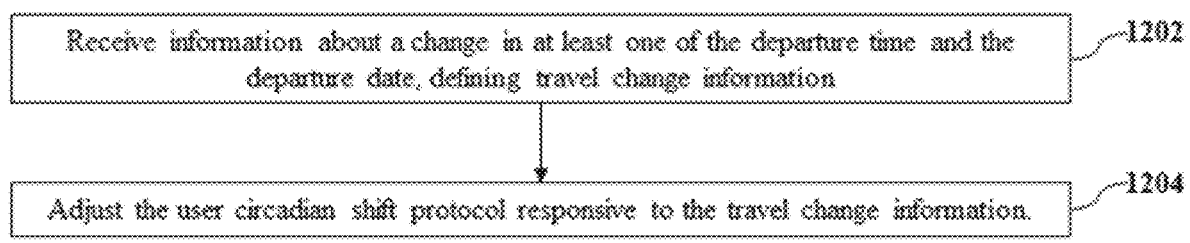
FIG. 12 is a flowchart illustrating a method of modifying a circadian shift protocol responsive to a travel delay according to an embodiment of the invention.

Referring now to FIG. 12, a method 1200 of modifying a circadian shift protocol responsive to a travel delay according to an embodiment of the invention is presented. The method 1200 may comprise receiving information about a change in at least one of a departure time, the departure date, the arrival time, and the arrival date defining travel change information 1202. Such a change is common with flights, trains, busses etc. being delayed or cancelled for a variety of reasons. Such an indication may be received in many ways, including, but not limited to, receiving an indication for the operator of the related travel mode, a calendar indication, or a user input. The method 1200 may further comprise adjusting the user circadian shift protocol responsive to the travel change information. Such an adjustment may include changing the time one or more activities is scheduled to be performed, adding or removing activities, changing when the complete circadian shift is accomplished, or any other aspect or element of the user circadian shift protocol.

Figure 13:
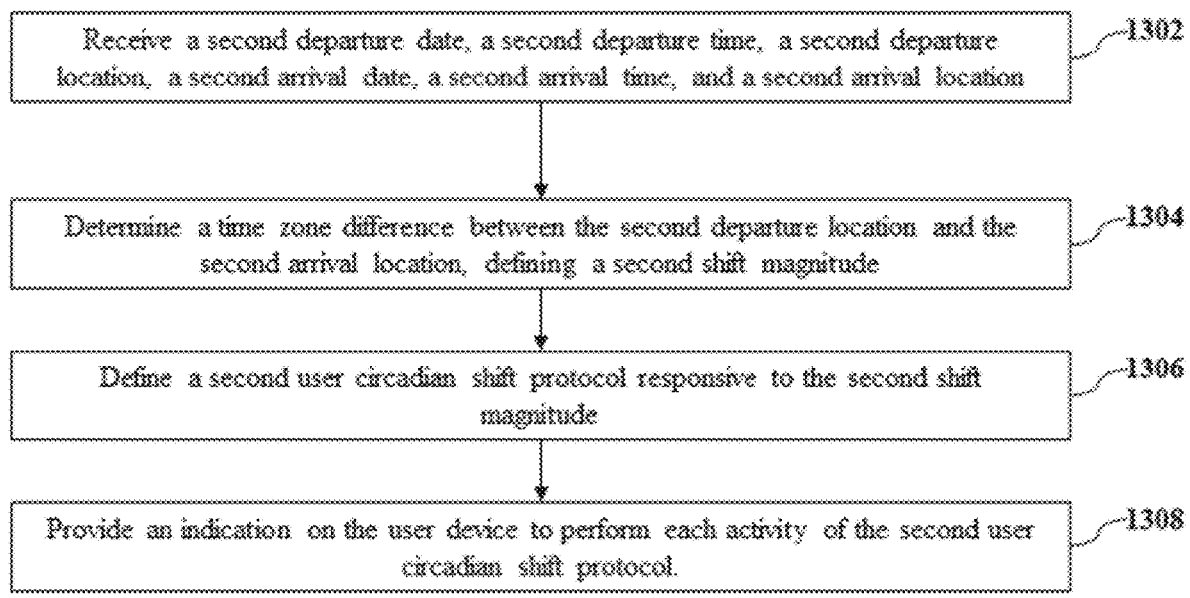
FIG. 13 is a flowchart illustrating a method of defining and displaying a second circadian shift protocol subsequent to a first circadian shift protocol according to an embodiment of the invention.

Referring now to FIG. 13, a method 1300 of defining and displaying a second circadian shift protocol subsequent to a first circadian shift protocol according to an embodiment of the invention is presented. In this embodiment, the user circadian shift protocol shown in FIG. 1 is a first user circadian shift protocol. The method 1300 may comprise receiving a second departure date, a second departure time, a second departure location, a second arrival date, a second arrival time, and a second arrival location 1302. In some embodiments, this information may be received as part of the user travel information. The method 1300 may further comprise determining a time zone difference between the second departure location and the second arrival location, defining a second shift magnitude 1304. The method 1300 may further comprise defining a second user circadian shift protocol responsive to the second shift magnitude 1306. The second user circadian shift protocol may comprise circadian-shifting activities as described hereinabove. The method 1300 may further comprise providing an indication on the user device to perform each activity of the second user circadian shift protocol 1308, as described hereinabove.

Figure 14:
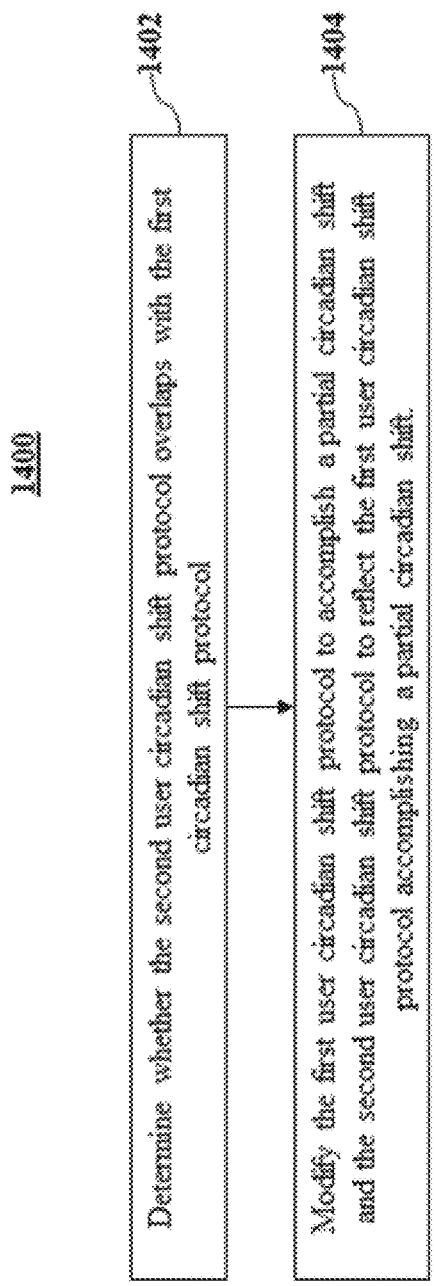
FIG. 14 is a flowchart illustrating a method of modifying the circadian shift protocols of FIG. 13 responsive to a conflict there between according to an embodiment of the invention.

Referring now to FIG. 14, a method 1400 of modifying the circadian shift protocols of FIG. 13 responsive to a conflict there between according to an embodiment of the invention is presented. The second circadian shift protocol may be understood as an intended circadian to occur subsequent to the first circadian shift protocol, but in close proximity by time. The method 1400 may comprise determining a length of stay defined as the time between the arrival time on the arrival date and the second departure time on the second departure date 1402. The method 1400 may further comprise determining whether the second user circadian shift protocol overlaps with the first circadian shift protocol. Such an overlapping may be based on whether the second user circadian shift protocol being shifting the user's circadian rhythm prior to the first circadian shift protocol accomplishing the full shift magnitude. The method 1400 may further comprise modifying the first user circadian shift protocol to accomplish a partial circadian shift and modifying the second user circadian shift protocol to reflect the first user circadian shift protocol accomplishing only a partial circadian shift, meaning second shift magnitude may be more or less than had the first user circadian shift protocol accomplished the full shift magnitude.

In some embodiments, the user circadian shift protocol may comprise an activity scheduled to be performed after the departure time and prior to the arrival time, i.e. during the flight.

Referring now to FIGS. 15-41, displays of an exemplary user interface 1500 showing the collection of information to generate a user circadian shift protocol and providing an indication of the protocol are presented. While the displays are travel-oriented, it is contemplated and included within the scope of the invention that any motivation for accomplishing a circadian shift may have a similar and according user interface that is within the scope of the invention.

Figure 15:
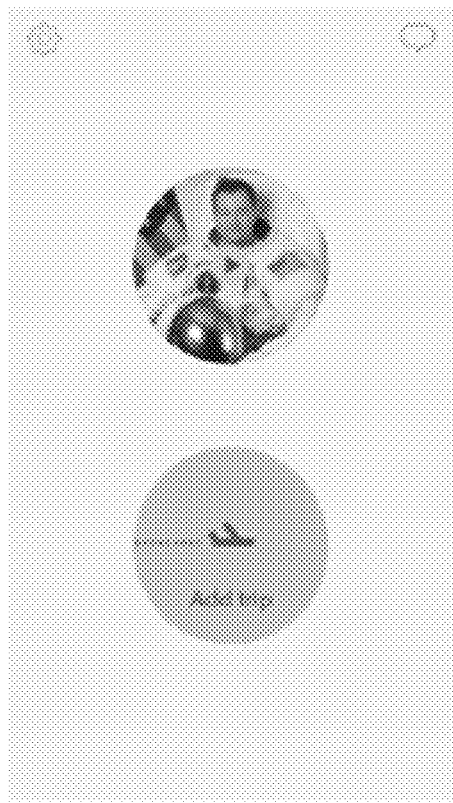
FIGS. 15-41 are illustrative graphical user interfaces of a method of receiving information for, defining, and displaying a circadian shift protocol according to embodiments of the invention.
Figure 16:
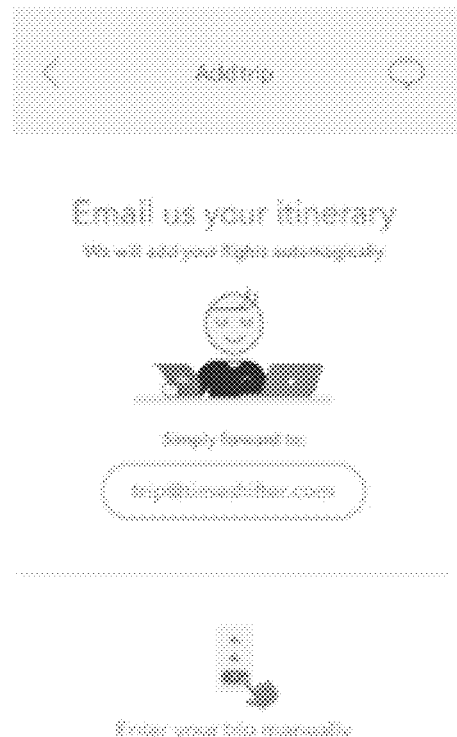
Figure 17:
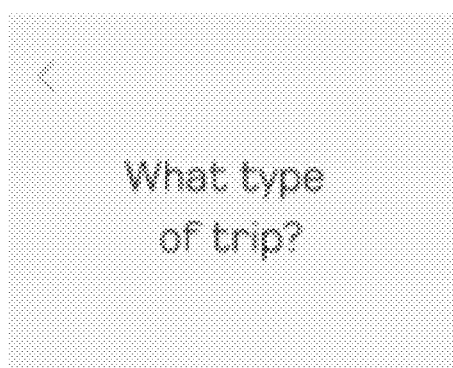
Figure 18:
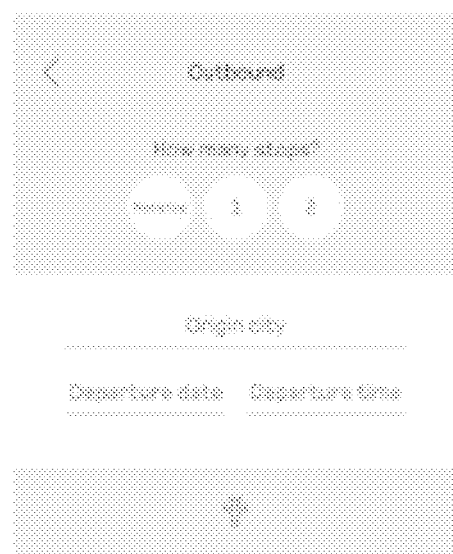
Figure 19:
Figure 20:
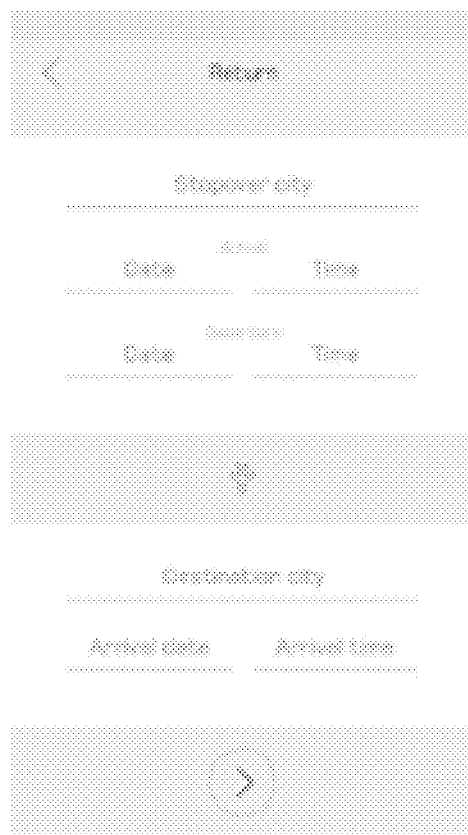
Figure 21:
Figure 22:
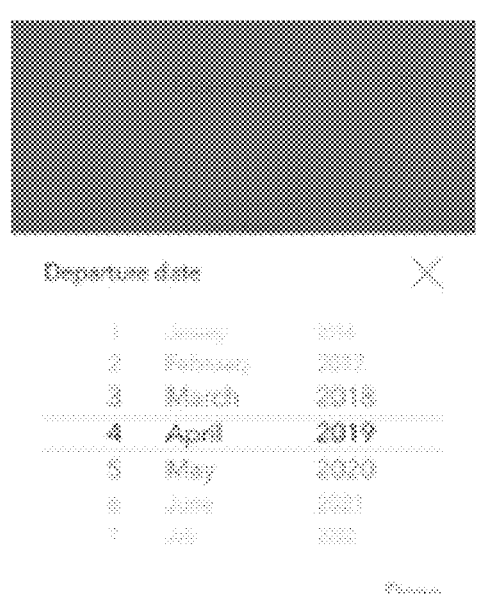
Figure 23:
Figure 24:
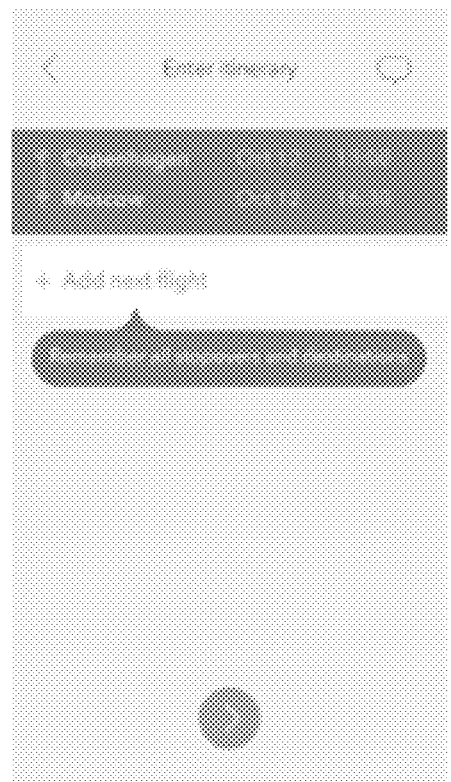

FIG. 15 depicts a display for providing the user the opportunity to provide a new indication of an intended circadian shift (a new trip). FIG. 16 provides an option for the user to provide travel information by email, with such an email being parsed to extract the relevant travel information, or to enter the travel information manually. FIGS. 17-24 present various screens for the user to enter travel information, including, but not limited to, departure date, departure time, departure location, stopover locations, stopover dates, stopover times, arrival date, arrival time, arrival locations, and flight information.

Figure 25:
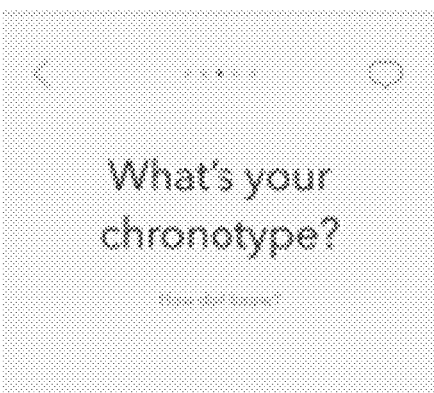
Figure 26:
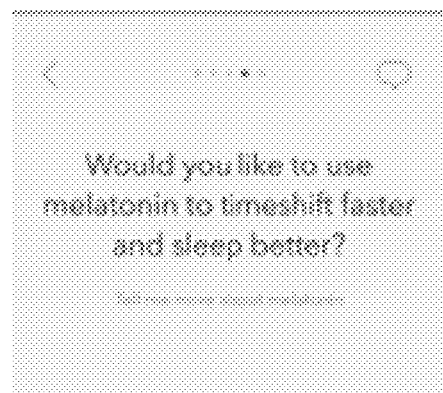
Figure 27:
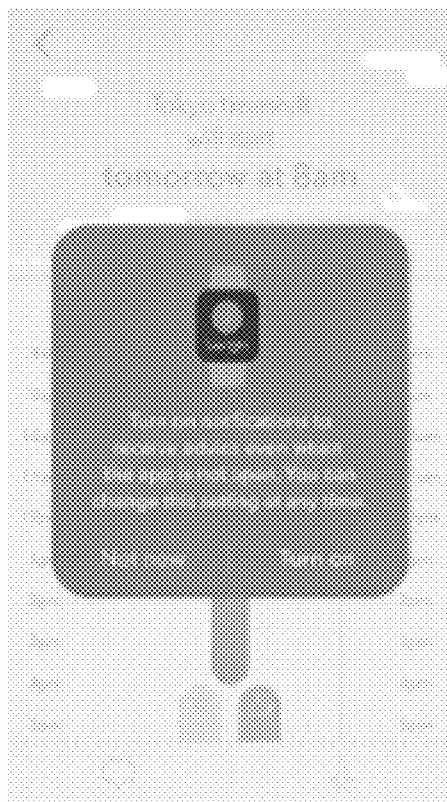
Figure 28:
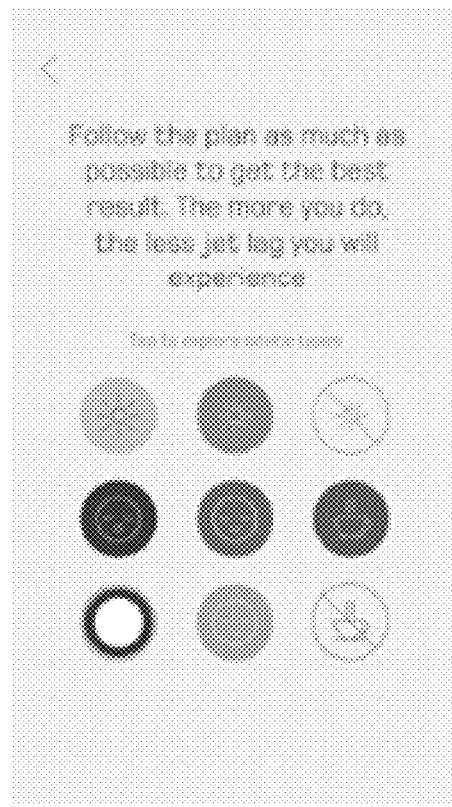
Figure 29:
Figure 30:
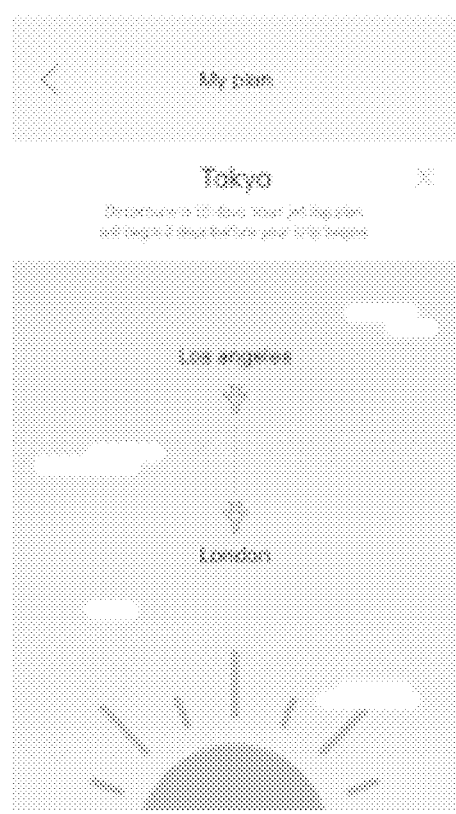
Figure 31:
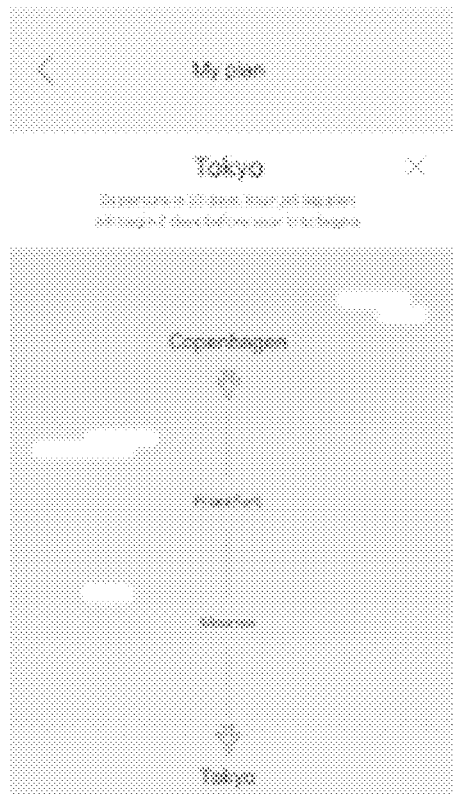
Figure 32:
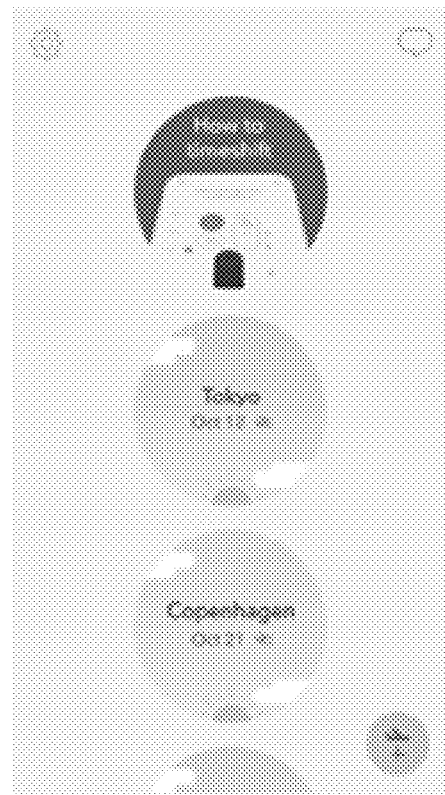

FIG. 25 presents a display to enable the user to indicate their chronotype (e.g. early bird, night owl, or neither). FIG. 26 presented a display to give the option for using chronobiotic substances (in this instance, melatonin) to facilitate the circadian shift, according to defining excluded activities as described herein above. FIG. 27 provides an indication to the user to configure an accessory device to facilitate provision of indications to perform the activities of the circadian shift protocol, in this instance, enabling notifications on a smart device, namely, a smart watch. FIG. 28 presents an overview of iconographic representation of various activities comprised by the circadian shift protocol.

Figure 33:
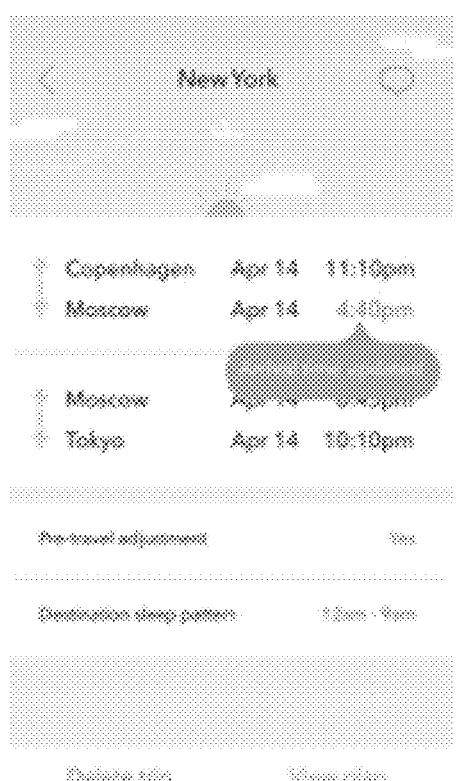

FIGS. 29-32 provide displays of summaries about the circadian shift protocol responsive to the travel information, including departure location and date, stopover locations, and arrival location and date. FIG. 33 presents receipt of an updated arrival time, according with travel change information recited herein above.

Figure 34:
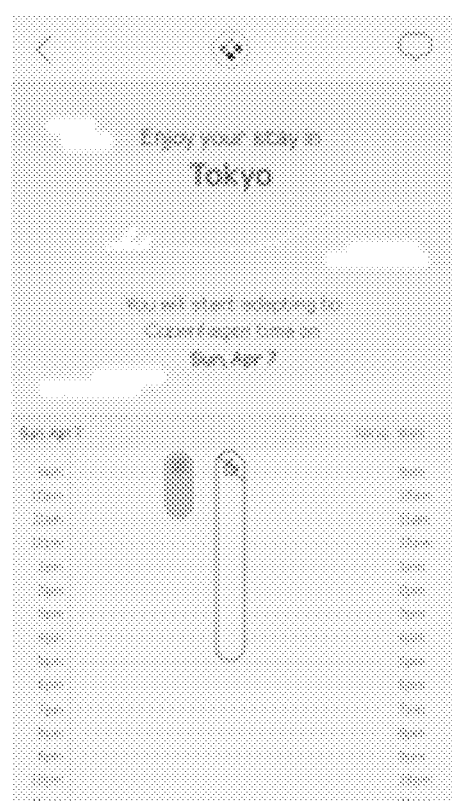
Figure 35:
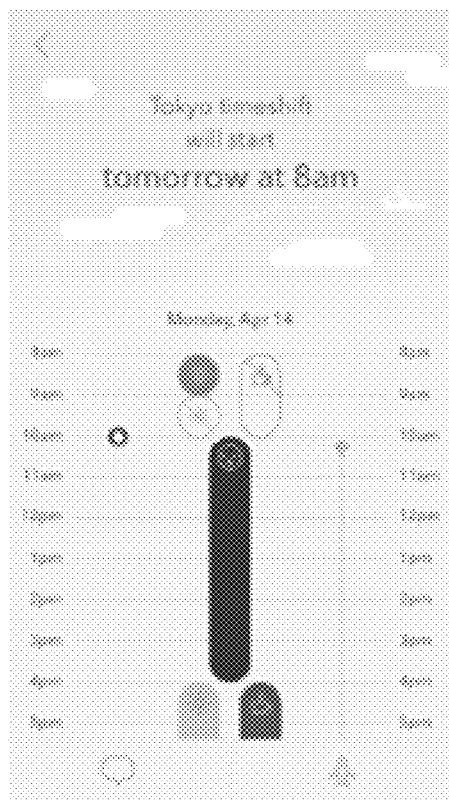
Figure 36:
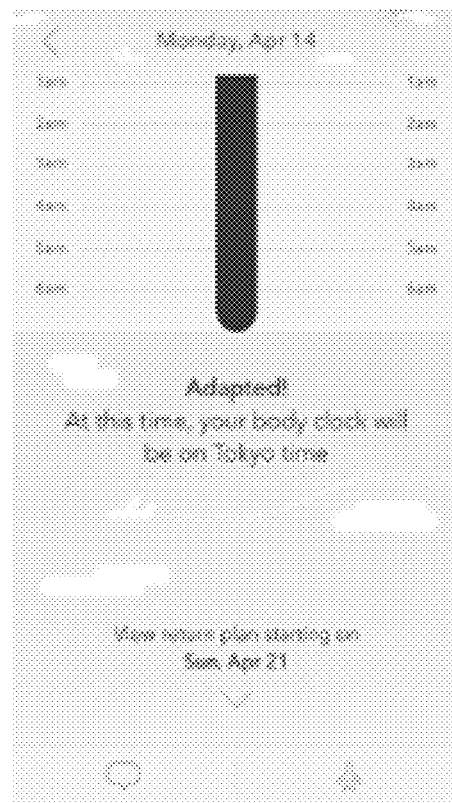
Figure 37:
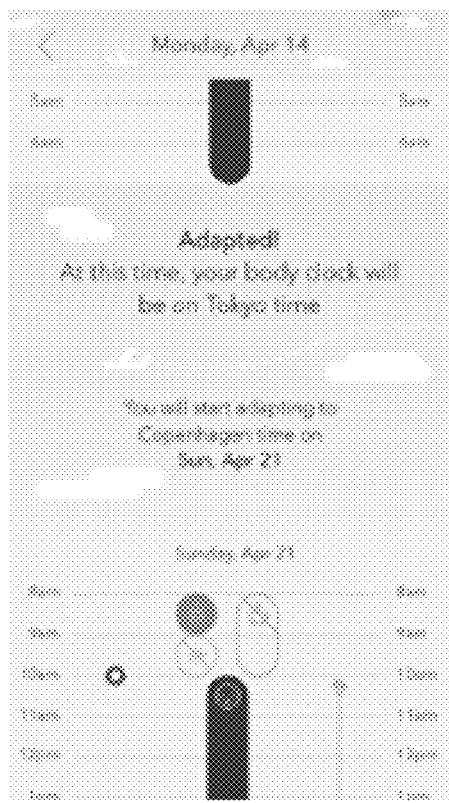
Figure 38:
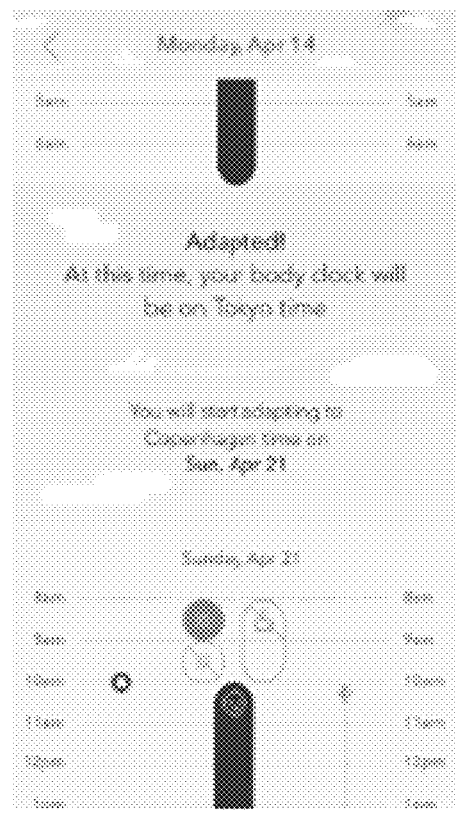
Figure 39:
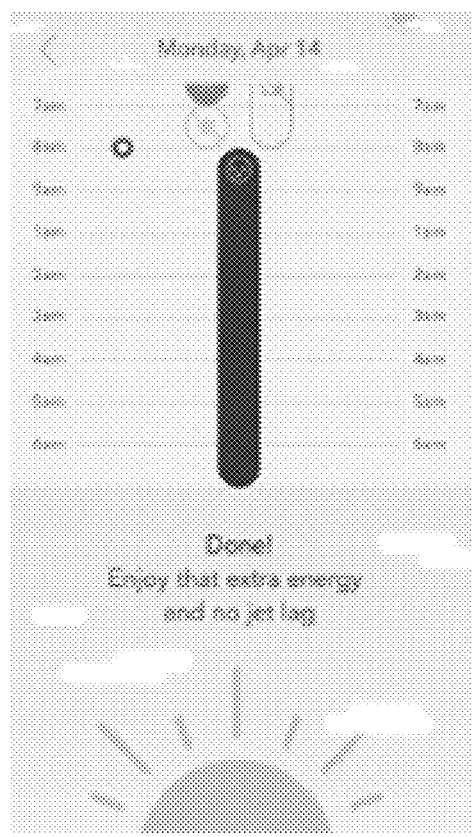
Figure 40:
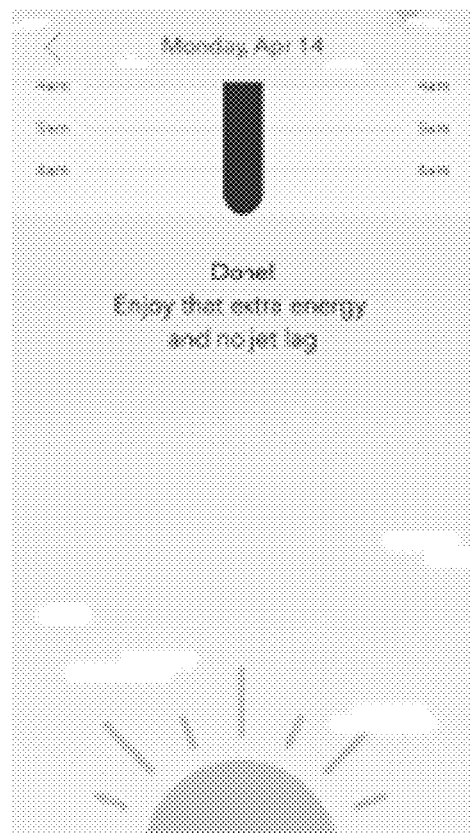
Figure 41:
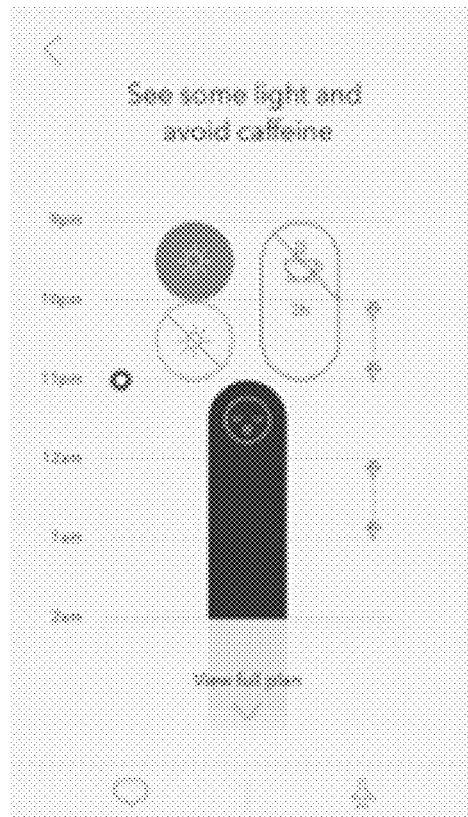

FIG. 34-36 present the provision of indications on the user device to perform activities of a circadian shift protocol, particularly the iconographic representation of the activities within a calendar to indicate the timing and duration of the activities. FIGS. 37-41 present the provision of indications on the user device to perform activities of a second circadian shift protocol that succeeds the protocol shown in FIGS. 34-36.

Figure 42:
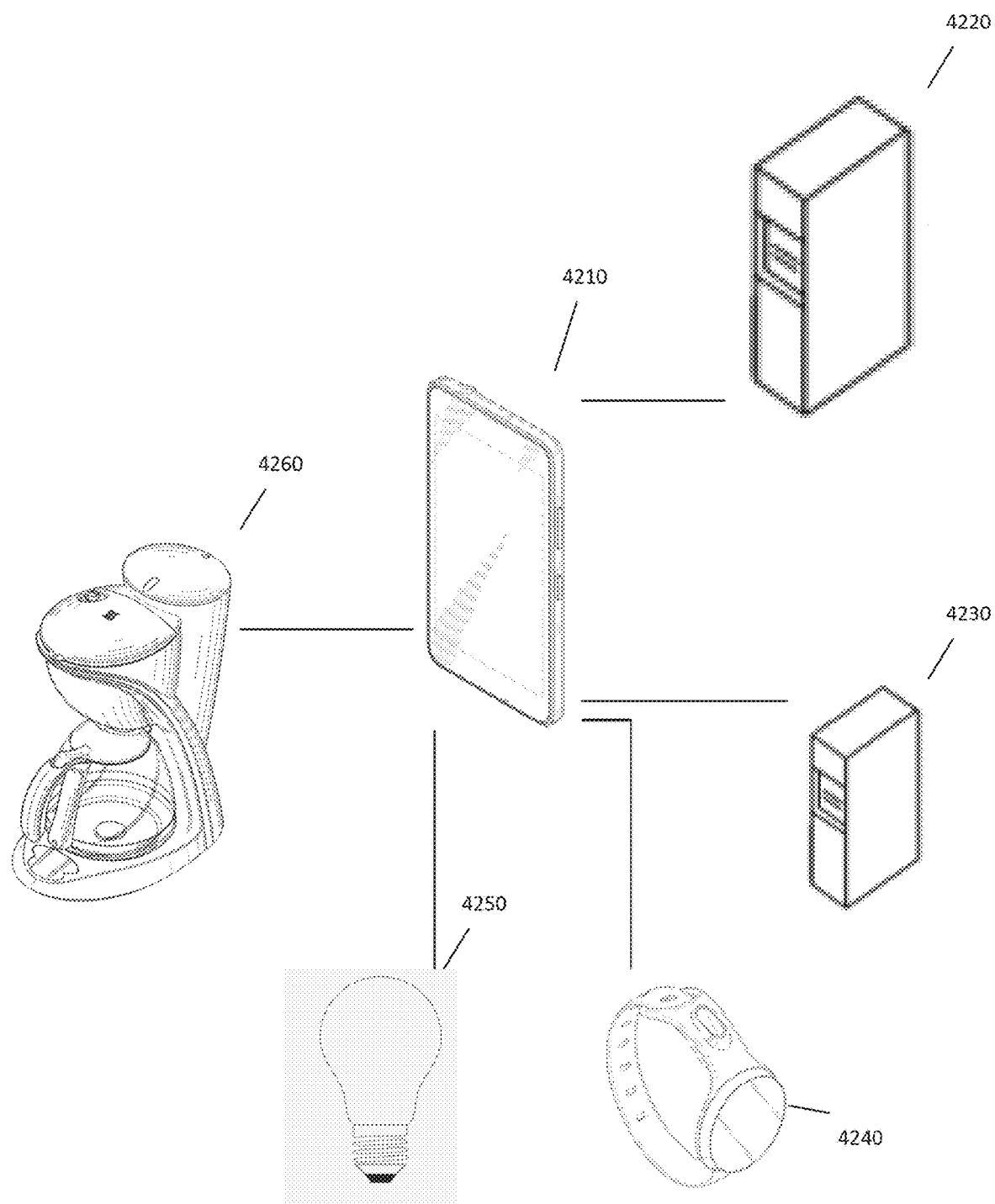
FIG. 42 is a schematic depiction of connected devices that may be part of the present invention.

Referring now to FIG. 42, a schematic representation of connected devices that may be part of the present invention is presented. As mentioned above, the method may be implemented on a user device 4210, which may be a smart phone. In some embodiments, the method may be implemented on a server 4220 which may be positioned in communication with the user device 4210, operable to provide display information to prompt the user to enter user inputs, to received user inputs, and to provide both a calendar display of a circadian shift protocol generated responsive to the user inputs and notifications on the user device 4210 according to the circadian shift protocol. Accordingly, the method may include sending a command to a device responsive to an activity comprised by a circadian shift protocol Additionally, at least one of the user device 4210 and the server 4220 may be positioned in communication with one or more attached devices, including, but not limited to, a third-party server 4230 that may be further attached to one or more smart devices, a smart watch 4240 that may receive and display circadian shift protocol notifications and calendar information, reformatted from how such information is delivered on the user device 4210 to account for the smaller screen or no screen, and the circumstances and context of the user. For example, a smart lamp 4250 in order to emit light having a spectral power distribution consistent with the circadian shift protocol (e.g. emitting light with greater intensity within the blue-light spectrum to simulate daylight, emitting light with less intensity in the blue-light spectrum to simulate avoiding daylight. In another example, a smart coffee maker 4260 may be communicated with to, for example, brew coffee when consuming caffeinated beverages is consistent with a circadian shift protocol, and deny brewing coffee when a circadian shift protocol recommends avoiding caffeinated beverages. In another example, a screen for crew members on an airplane display circadian shifting protocols of passengers, the passengers' needs based on their circadian shift protocols, and their compliance with the circadian shifting protocols, enabling the crew to personalize the timing of in-flight activities such as meal service, appropriate lighting, availability of coffee/tea/caffeine, melatonin, etc. consistent with such circadian shift protocols. In another example, an in-flight entertainment system display activities, exposures, and substance ingestions of a passenger's circadian shift protocol allowing the passenger to take recommended actions and maybe also use the system to order supportive products or services, including the ordering of coffee/tea/caffeine, melatonin, etc.

The circadian shifting protocol may 'run' the screen brightness and spectrum (e.g. reduce or increase the proportion of short wavelength blue light emitted by the screen) of any electronic device, including a computer, phone, or in-flight entertainment system on an airplane or in any other setting by altering the display characteristics of displays, altering the light emission characteristics of lighting devices. Further, the circadian shifting protocol may 'run' the auxiliary/overhead/seat/ambient lighting or even the window screens (either automatically pulling them up or down or filtering the intensity and spectrum of light that is transmitted) or window glass (automatically altering the filtering the intensity and spectrum of light that is transmitted). Reminders and notifications could also be presented on the screens for what to do and when based on the circadian shift protocol, taking the form of causing the display of information on a display.

Additionally, the circadian shifting protocol could 'run' the brightness and spectrum (e.g. reduce or increase the proportion of short wavelength blue light emitted by the screen) of hotel room lighting or even the window screens (either automatically pulling them up or down or filtering the intensity and spectrum of light that is transmitted) or window glass (automatically altering the filtering the intensity and spectrum of light that is transmitted).

If the individual wishes to follow such activities, exposures, and substance ingestion on any device, the device may offer options to support the individual in being compliant with such efforts. For example, if the user agrees to go to sleep, a movie playing on an in-flight entertainment system could be paused and an alarm clock offered to help the passenger wake up when the circadian shift protocol determined it would be optimal to wake up).

However, if the individual does wish to follow such activities, exposures, and substance ingestion, alternative suggestion may be offered to avoid impacting the circadian shift negatively (e.g. lower the brightness and a better spectrum), minimizing the negative impact when a passenger for example continues to watch a movie when they were supposed to avoid light entirely.

While the number of time zones to be crossed (and the jet lag adaptation required) will be the same for different versions of a given trip, there is variability in the degree to which the flight affects sleep patterns and the degree to which an individual can comply with the advice. In some embodiments, communication of one of the user device 4210 and the server 4220 with the third-party server 4230 may comprise identifying one or more flights that are relatively more conducive to avoiding jet lag/accomplishing a circadian shift. This may take the form of either providing a time range when it would be most conducive to the circadian shift protocol to travel, or further conducting a search of available commercial passenger flights within such a time range to provide the user with a variety of travel options that will best match the circadian shift protocol.

Figure 43:
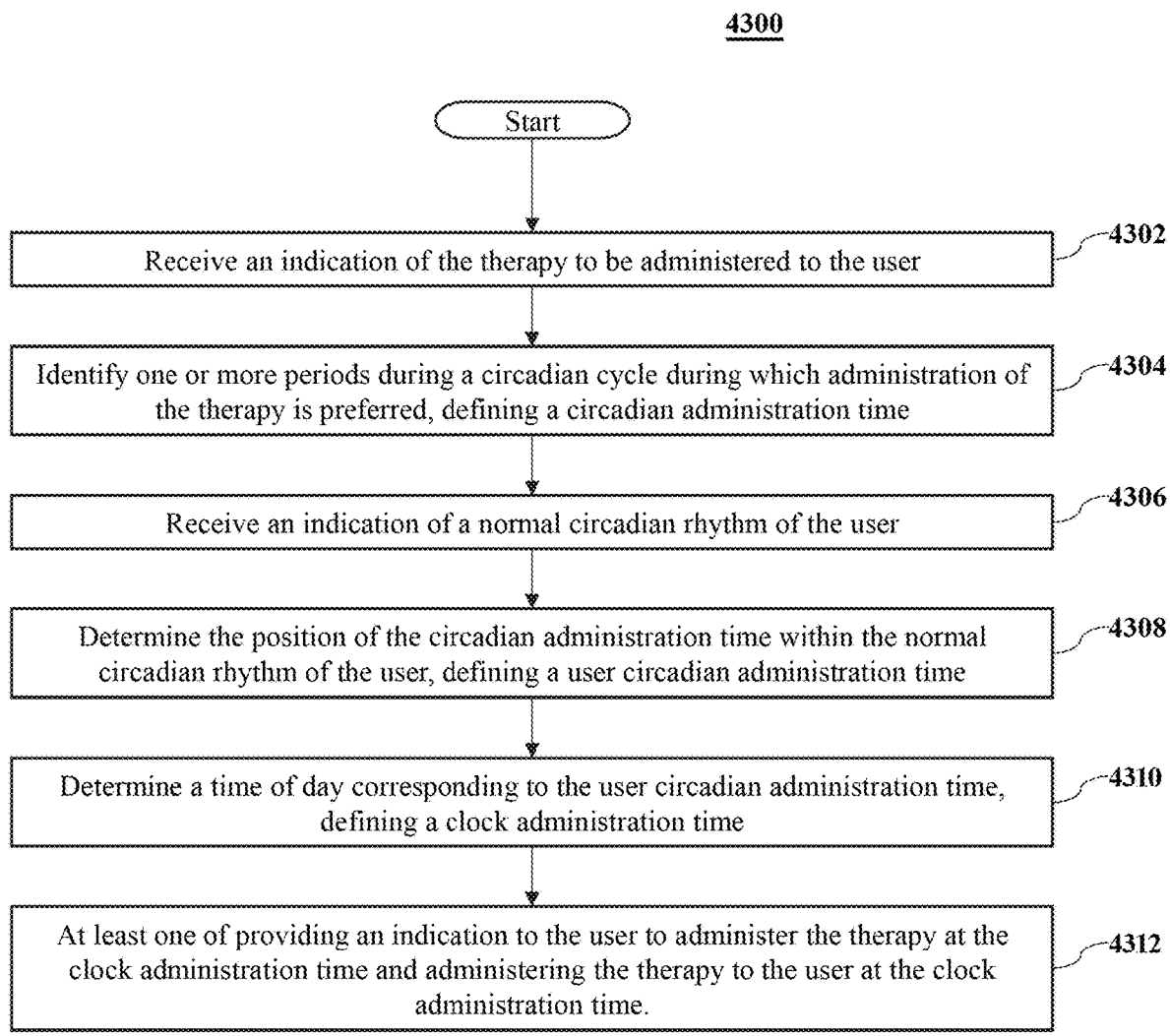
FIG. 43 is a flow chart illustrating a method according to an embodiment of the invention.

Referring specifically to FIG. 43, a method 4300 of determining and administering therapies responsive to a circadian rhythm of a patient is presented. The method may include receiving an indication of the therapy to be administered at 4302. As noted above, the therapy may be any type of therapy intended to have a therapeutic effect, including, but not limited to, the administration of medication, vaccines, and other pharmaceutical products, and other therapies such as chemotherapy and surgery.

Upon receiving the indication of the therapy to be administered, the method 4300 may continue at 4304 with identifying one or more periods during a circadian cycle during which administration of the therapy is preferred. The identified periods may be defined as a circadian administration time. Such identification may be accomplished by querying a database of therapies with the received therapy to be administered and receiving a response indicating the period during the circadian cycle which that particular therapy is most efficacious. Examples of such periods may include one or more phases during the circadian rhythm, such as sleep phase and/or wake phase, as well as positions within different phases, such as early, middle, or late within the respective phases. These positions within the circadian rhythm are exemplary only and all possible characterizations of the phases of the rhythm are contemplated and included within the scope of the invention.

The method 4300 may at 4306 continue with receiving an indication of a normal circadian rhythm of the user. Such a normal circadian rhythm may conform to one of the standard types of rhythms identified, including a rhythm that conforms to a typical sleep-wake cycle, so-called "night owl" rhythms with later wake-up and going to sleep times compared to a typical sleep-wake cycle, so-called "early bird" rhythms with earlier wake-up and going to sleep times compared to a typical sleep-wake cycle, cycles with comparatively shorter or longer sleep phases, cycles with comparatively shorter or longer wake phases, cycles with sporadic or inconsistent sleep-wake cycles, and combinations thereof, commonly referred to as chronotype. This indication may include an indication of when the user wakes up, when the user goes to sleep, when the user is typically awake, when the user is typically a sleep, whether the user is a night owl, an early bird, or has a typical circadian pattern, their light-dark exposure, and the like. Additional indications may be the user's sex, age, present time zone, future time zone, present work shift, future work shift, heart rate, heart rate variability, core body temperature, skin temperature, and any other biological marker as is known in the art.

As is known in the art, there are several circadian clocks for an individual. The central circadian rhythm is governed by the central suprachiasmatic nucleus (SCN) of the hypothalamus, but there are several so-called peripheral circadian clocks that exist in various other tissues in an individual and are synchronized by the SCN, including, but not limited to, the liver, kidney, lung, fibroblasts, glands, including submandibular glands, and the like. It is contemplated and included within the scope of the invention that the normal circadian rhythm of the user may be at least one of the central circadian rhythm and a peripheral circadian rhythm.

The method 4300 may continue at 4308 with determining the position of the circadian administration time within the normal circadian rhythm of the user, defining a user circadian administration time. Where the user has a standard circadian rhythm, with typical sleep-wake cycles in terms of length and time of day, there may be no difference in the circadian administration time and the normal circadian rhythm, i.e. the circadian administration time may occur at a typical time within the normal circadian rhythm. Where the normal circadian rhythm of the user deviates from a typical circadian rhythm, the position of the circadian administration time may similarly deviate from its position within a normal circadian rhythm. For example, it may be possible that the circadian administration time is relative to a hormonal change in the user, for example, the therapy is most efficacious when administered one hour after a hormonal increase. Furthermore, a user's normal circadian rhythm may be abnormal in that the hormonal increase occurs at an unusual time within their circadian rhythm. Accordingly, the circadian administration time may be different for that user when compared to an individual with a typical circadian rhythm. Other physiological changes tied to circadian rhythms are contemplated and included within the scope of the invention, including, but not limited to, blood glucose level, body temperature, and the like.

The method 4300 may continue at 4310 with determining a time of day corresponding to the user circadian administration time, defining a clock administration time. This step may produce a time during the day during which the therapy may be administered for maximum efficacy. Accordingly, the clock administration time is the time shown on the clock when the therapy may be administered, e.g. 9:00 a.m., 13:00, etc. Crucially, the clock administration time is determined responsive to the user circadian administration time which is itself responsive to the normal circadian rhythm of the user. Accordingly, user's receiving the same therapy that have different normal circadian rhythms may have different clock administration times, as the maximum efficacy period of their respective circadian rhythms occur at different points in time during the day.

Finally, the method 4300 may conclude at 4312 with performing an additional action that may take many forms, including providing an indication to the user to administer the therapy at the clock administration time and administering the therapy to the user at the clock administration time. The notification may take many forms, including all possible methods of conveying information to the user. In some embodiments, this may include operating a device that provides audio, visual, and/or combinations thereof to convey the information. In some embodiments, this may include operating a display device to provide text or illustration that conveys the clock administration time for the therapy, for example, displaying the therapy to be provided and the clock administration time for the therapy. In some embodiments, this may include operating a sound-generating device to provide an audible indication of the clock administration time that may include announcing the time, announcing the therapy to administer, and a tonal indication that is associated with the therapy/clock administration time. In some embodiments, the indication may include transmitting a message to a remote computerized device to provide an indication on the remote computerized device indicating the clock administration time. This may include one or more of sending a command to an application running on the remote computerized device, such as a push notification, sending a text message complying with a known text messaging protocol, for example, short message service (SMS), multimedia messaging service (MMS), enhanced messaging service (EMS), rich communication service (RCS), and the like. This may further include sending an e-mail to an e-mail address associated with the user. This may further include interacting with a remote computerized device operable to provide an audio indication as described above, such as a smart home device, including, but not limited to, Amazon Echo devices, Google Home devices, and Apple Homepod devices.

It is further contemplated and included within the scope of the invention that multiple indications may be provided to the user regarding administration of the therapy at the clock administration time. For example, one or more indications may be provided to the user in advance of the clock administration time so that the user has time to prepare for therapy administration, either separate from or in addition to an indication occurring at the clock administration time.

In some embodiments, administering the therapy may include operating one or more devices configured to facilitate the administration of the therapy. This may include any device that either facilitates the administration of therapy and/or administers therapy. Some embodiments may include operating a device that provides access to medication, vaccines, or other pharmaceuticals materials. Such access may include dispensing the materials from a secured location that is inaccessible to a location that is accessible, unlocking or opening a container containing the materials so that they become accessible, and the like. Some embodiments may include administering the therapy, including, for example, operating a material-dispensing machine such as a medication-dispensing pump to inject the medication into the patient, operating a machine that performs the therapy, for example performs physical therapy, irradiates the patient with therapeutic radiation, and the like, and all other therapy-delivery devices as are known in the art.

Figure 44:
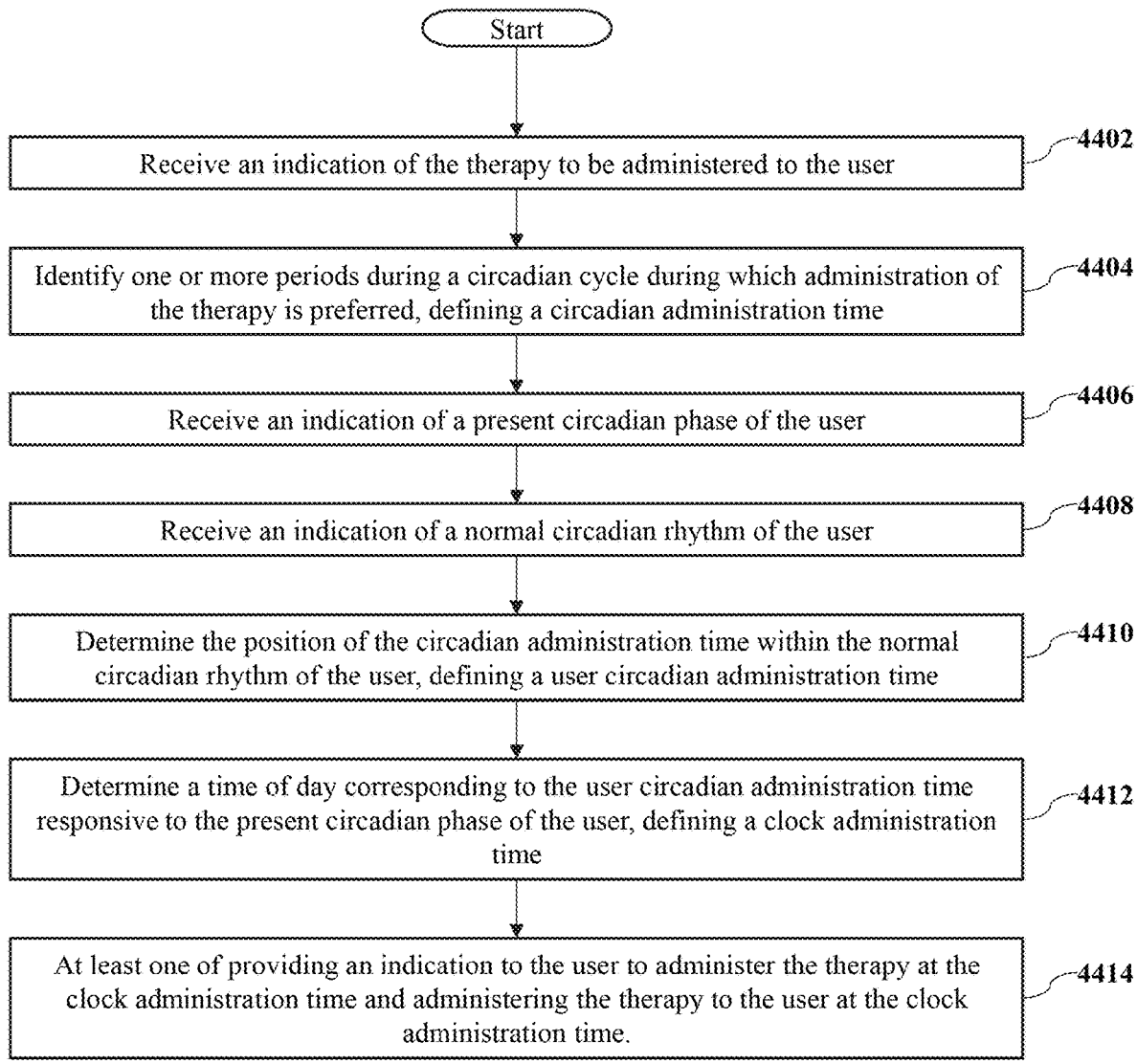
FIG. 44 is a flow chart illustrating another method according to an embodiment of the invention.

Referring now to FIG. 44, a method 4400 according to another embodiment of the invention is presented. The method 4400 may include steps similar to those of the method 4300 of FIG. 43, including receiving an indication of the therapy to be administered to the user at 4402 and identifying one or more periods during a typical circadian cycle during which administration of the therapy is preferred, defining a circadian administration time at 4404. The method 4400 may continue at 4406 with receiving an indication of a present circadian phase of the user. This may indicate at what point in their circadian rhythm the user is presently in. Such an indication may include a physical or physiological measurement, including, but not limited to, body temperature, such as a minimum core body temperature, measured hormone levels such as melatonin, cortisol, and/or adrenocorticotropic hormone (ACTH), blood glucose level, and the like. Such an indication may also include when and how long the user has been awake, when and how long the user most recently slept, when and how much circadian cycle-affecting substances the user has ingested (such as caffeine, melatonin supplements, and the like), when and the extent of recent exercise of the user, and the like, and when and what the user has most recently eaten for nutrition. These examples are for illustrative purposes only and do not limit the scope of types of indications contemplated by the invention.

The method 4400 may continue at 4408 with receiving an indication of a normal circadian rhythm of the user, as described above, and at 4410 with determining the position of the circadian administration time within the normal circadian rhythm of the user, defining a user circadian administration time. The method 4400 may continue at 4412 with determining a time of day corresponding to the user circadian administration time, defining a clock administration time. In this embodiment, the clock administration time is determined responsive to the present circadian phase of the user. This may facilitate determining a clock administration time that is more accurate based on the circadian rhythm of the user for that day, instead of relying only on the normal circadian rhythm for the user. Accordingly, this results in the therapy being administered as closely as possible to the circadian administration time as possible while accounting for the day-to-day variations in the circadian rhythm of individuals.

The method 4400 may conclude at 4414 with at least one of providing an indication to the user to administer the therapy at the clock administration time and administering the therapy to the user at the clock administration time.

Figure 45A:
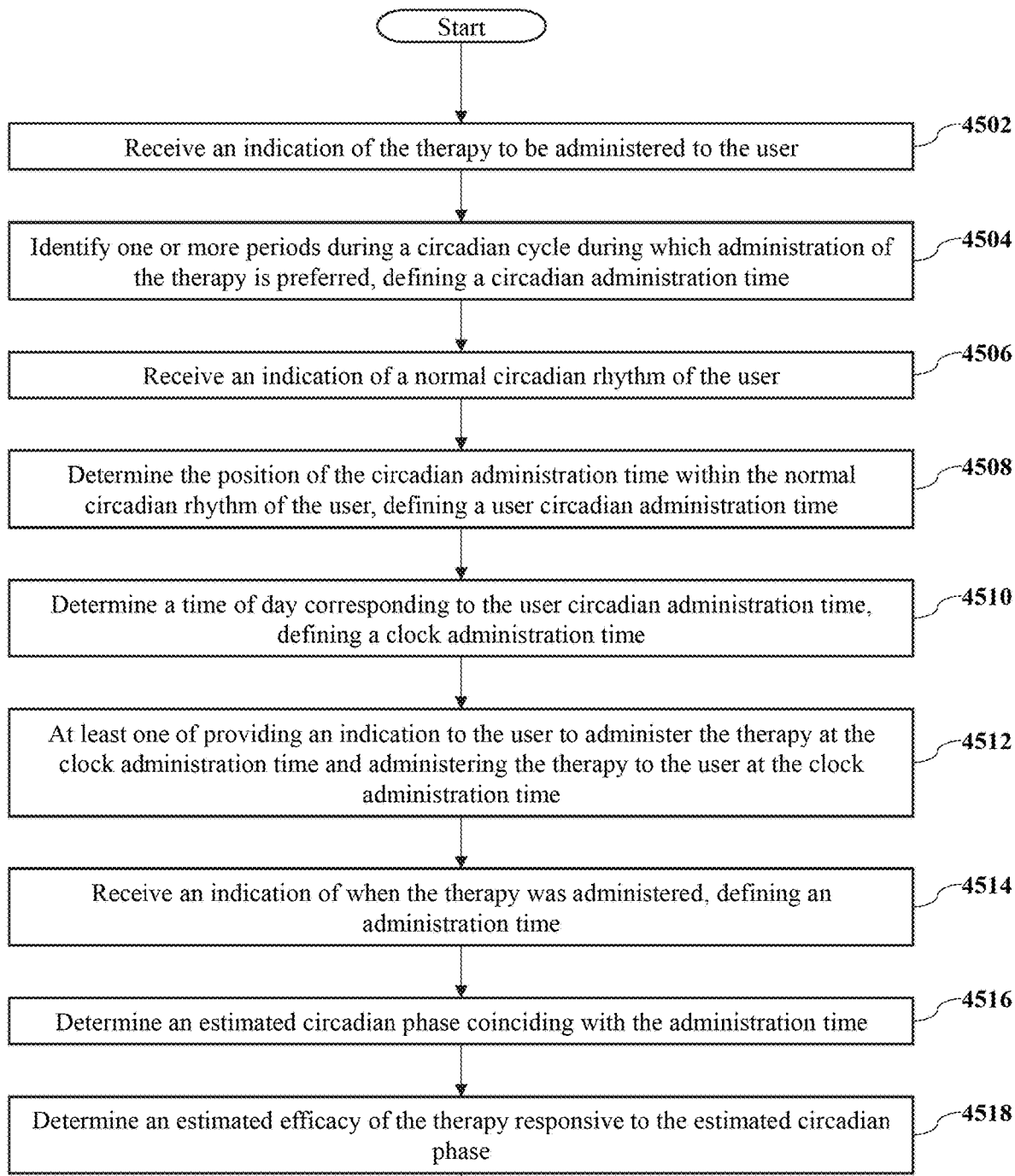
FIGS. 45A-B are flow charts illustrating another method according to an embodiment of the invention.
Figure 45B:
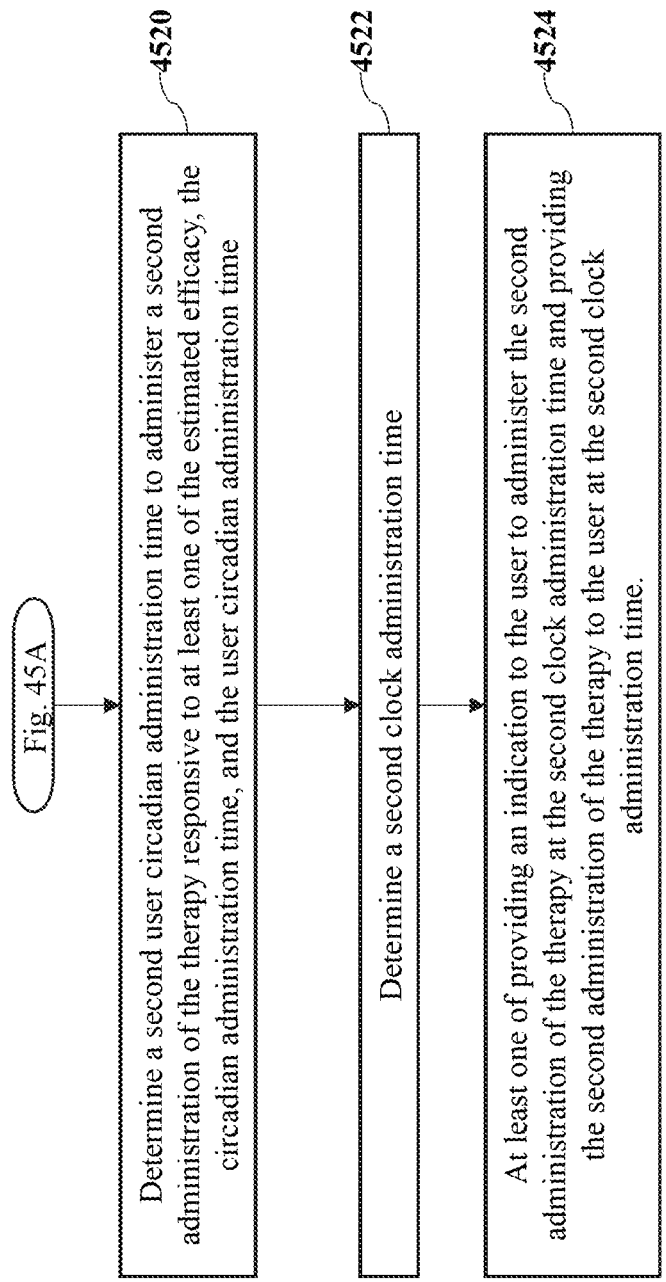

Referring now to FIGS. 45A-B, a method 4500 according to another embodiment of the invention is presented. The method 300 may include many of the steps of the method 4300 of FIG. 43, including receiving an indication of the therapy to be administered to the user at 4502, identifying one or more periods during a typical circadian cycle during which administration of the therapy is preferred, defining a circadian administration time at 4504, and receiving an indication of a normal circadian rhythm of the user at 4506. The method 4500 may then continue at 4508 with determining a time of day corresponding to the user circadian administration time, defining a clock administration time, and at 4512 with at least one of providing an indication to the user to administer the therapy at the clock administration time and administering the therapy to the user at the clock administration time.

The method 4500 may continue at 4514 with receiving an indication when the therapy was administered, defining an administration time. The indication may include various types of information, including, but not limited to, and indication when the therapy was performed, when the therapy started, when the therapy was completed, the duration of the therapy, and a quantification of some aspect of the therapy, such as a dosage of medication administered, a dosage of radiation administered, a length of time of performing a type of physical therapy or therapeutic exercise, and the like, and a qualification of some aspect of the therapy, such as the relative quality (e.g. excellent, good, fair, poor) of the therapy that was administered.

The method 4500 may continue at 4516 with determining an estimated circadian phase coinciding with the administration time. This estimation may be made responsive to the administration time and the normal circadian rhythm received at 306. As described above, the efficacy or other desirable trait of a therapy can vary significantly by when in the circadian rhythm it is administered. Accordingly, after determining the estimated circadian phase coinciding with the administration time, the method 4500 may continue at 4518 with determining an estimated efficacy of the therapy responsive to the estimated circadian phase. The estimated efficacy may be determined responsive to the administration time. Moreover, the database of therapies described above may be queried if it is determined the administration time is outside one or both of the circadian administration time and the user circadian administration time. In such embodiments, the database may have information about the efficacy of therapies when administered in circadian phases other than the preferable circadian phase.

The method 4500 may continue at 4520 with determining a second user circadian administration time to administer a second administration of the therapy responsive to at least one of the estimated efficacy, the circadian administration time, and the user circadian administration time. The circadian timing of the second user circadian administration time may be calibrated to compensate for the less-than-completely efficacious first administration of the therapy. For example, the second administration of the therapy may be necessary because of the estimated efficacy being under a threshold efficacy. The threshold efficacy may be a minimum efficacy necessary for adequate therapeutic effect of the therapy. Accordingly, in some embodiments the second user circadian administration time may be selected for a period during the user's circadian rhythm that is not maximally efficacious, so that there is not too much of the effect caused by the therapy than is desirable. In some embodiments, the second user circadian administration time may be the next in time most efficacious period during the user's circadian rhythm within the same day to have sufficient therapeutic effect within the single circadian cycle. Alternatively, the second administration of the therapy may be part of a prescribed course of treatment, but may nonetheless be selected based on the efficacy of the first administration of the therapy. Furthermore, it is contemplated and included within the scope of the invention that modifications to the therapy, i.e. differences between the first and second administrations of the therapy may also be determined. Examples of such modifications include increasing or reducing the amount of therapeutic substance that is delivered to the patient, changing the length or intensity of administration of a therapy, and the like.

The method 4500 may continue at 4522 with determining a second clock administration time responsive to the second user circadian administration time and at 4524 with at least one of providing an indication to the user to administer the second administration of the therapy at the second clock administration time and providing the second administration of the therapy to the user at the second clock administration time.

Figure 46A:
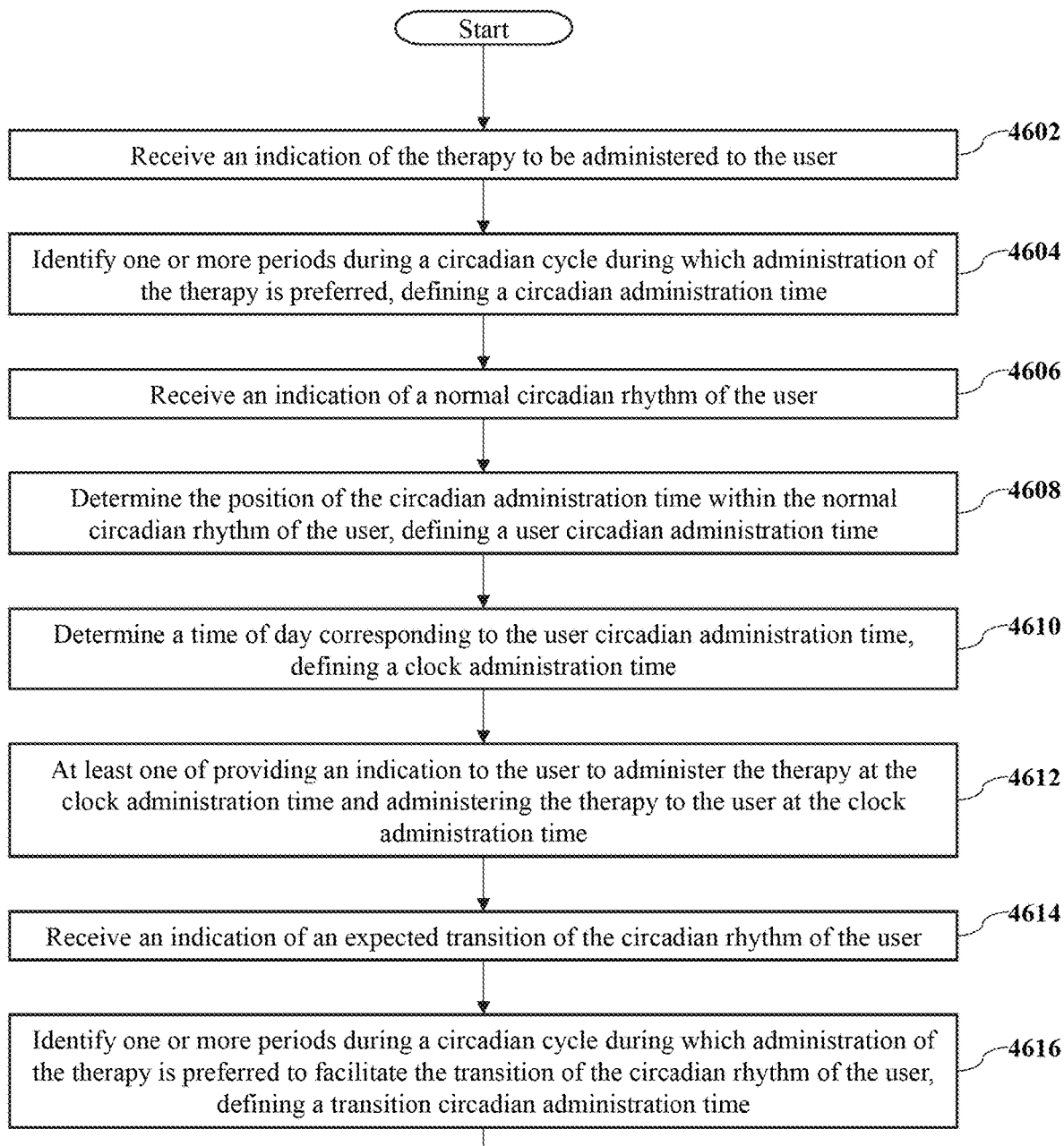
FIGS. 46A-B are flow charts illustrating another method according to an embodiment of the invention.
Figure 46B:
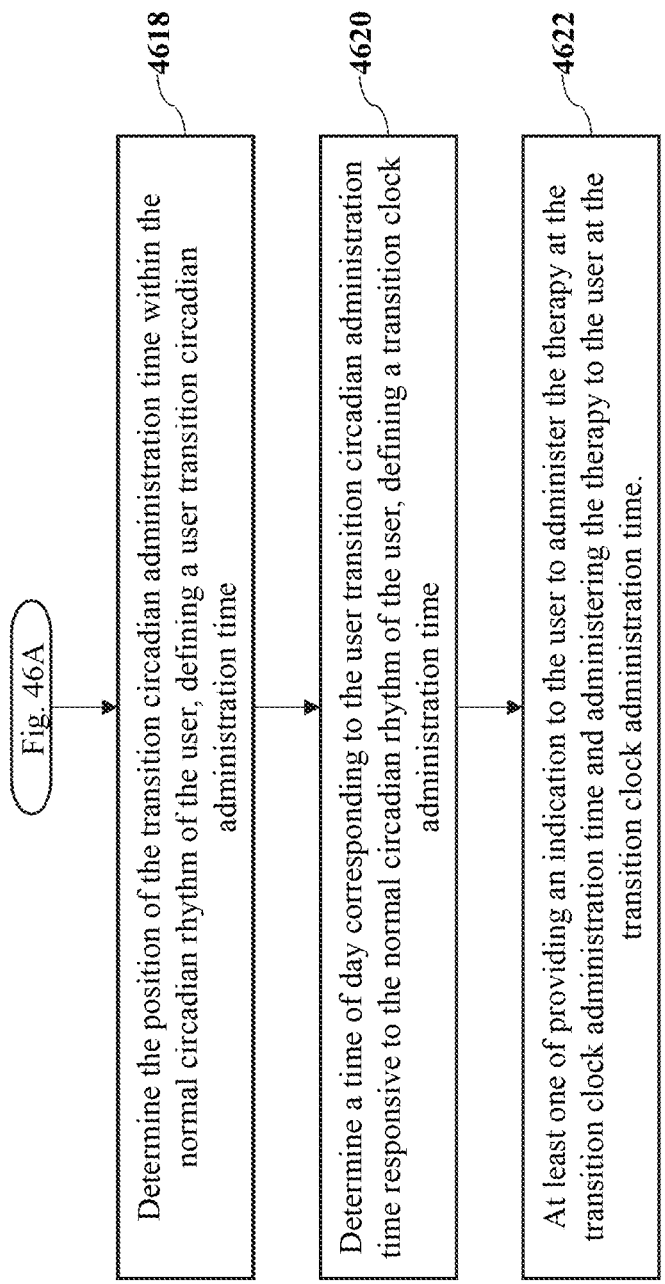

Referring now to FIGS. 46A-B, a method 4600 according to an embodiment of the invention is presented. The method 4600 may be similar to method 4300 of FIG. 43, including receiving an indication of a therapy to be administered to the user at 4602, identifying one or more period during a circadian cycle during which administration of the therapy is preferred, defining a circadian administration time at 4604, receiving an indication of a normal circadian rhythm of the user at 4606, determining the position of the circadian administration time within the normal circadian rhythm of the user, defining a user circadian administration time, at 4608, determining a time of day corresponding to the user circadian administration time, defining a clock administration time, at 4610, and at least one of providing an indication to administer the therapy at the clock administration time and administering the therapy to the user at the clock administration time at 4610. The method 4600 may continue at 4614 with receiving an indication of an expected transition of the circadian rhythm of the user. The expected transition of the circadian rhythm may be any event or cause that may effectuate a change in the circadian rhythm of the user, including, but not limited to, upcoming travel or move to a different time zone for the user, an upcoming change to the sleep schedule for the user for whatever reason, including a change in the work schedule (e.g. changing to a night shift where the user works during the night hours and sleeps during the day), an anticipated change to the circadian rhythm originating with starting or terminating an activity or therapy that changes the user's circadian rhythm (e.g. starting or stopping taking medication that changes the sleep habits of the user), and the like. The indication of the expected transition may indicate both the direction of the circadian shift (e.g. rising earlier or later) and/or the magnitude of the circadian shift (e.g. how much earlier/later rising occurs).

The method 4600 may continue at 4616 with identifying one or more periods during a circadian cycle during which administration of the therapy is preferred to facilitate the transition of the circadian rhythm of the user, defining a transition circadian administration time. Accordingly, any effect administration of the therapy may have may be identified and considered to determine when to administer the therapy so as to assist the user in transitioning to the new circadian rhythm. In some instances, where the therapy has no circadian effect, the transition circadian administration time may be the same as the circadian administration time. However, where the therapy has a circadian effect, that effect may be utilized to help the user shift to the new circadian rhythm. Additional information regarding identifying when to administer therapies to effectuate a circadian shift may be found above. The information about the circadian effect the therapy will have may be obtained similar to identifying the preferred circadian point/phase to administer the therapy, by querying a database containing such information and receiving an indication as to the circadian effect of the therapy.

The method 4600 may continue at 4618 with determining the position of the transition circadian administration time within the normal circadian rhythm of the user, defining a user transition circadian administration time. This may be performed responsive to the indicated circadian shift the therapy will affect. For example, if the therapy will have an advance effect and the transition is an advance, the user transition circadian administration time may be at the same time or earlier than the user circadian administration time. As another example, if the therapy will have a delay effect and the transition is a delay, the user transition circadian administration time may be at the same time or later than the user circadian administration time. These scenarios are exemplary only and any combination of advances and delays and user transition circadian administration times responsive thereto are contemplated and included within the scope of the invention.

The method 4600 may continue at 4620 with determining a time of day corresponding to the user transition circadian administration time responsive to the normal circadian rhythm of the user, defining a transition clock administration time, and at 4620 with at least one of providing an instruction to the user to administer the therapy and administering the therapy to the user at the transition clock administration time.

Figure 47B:
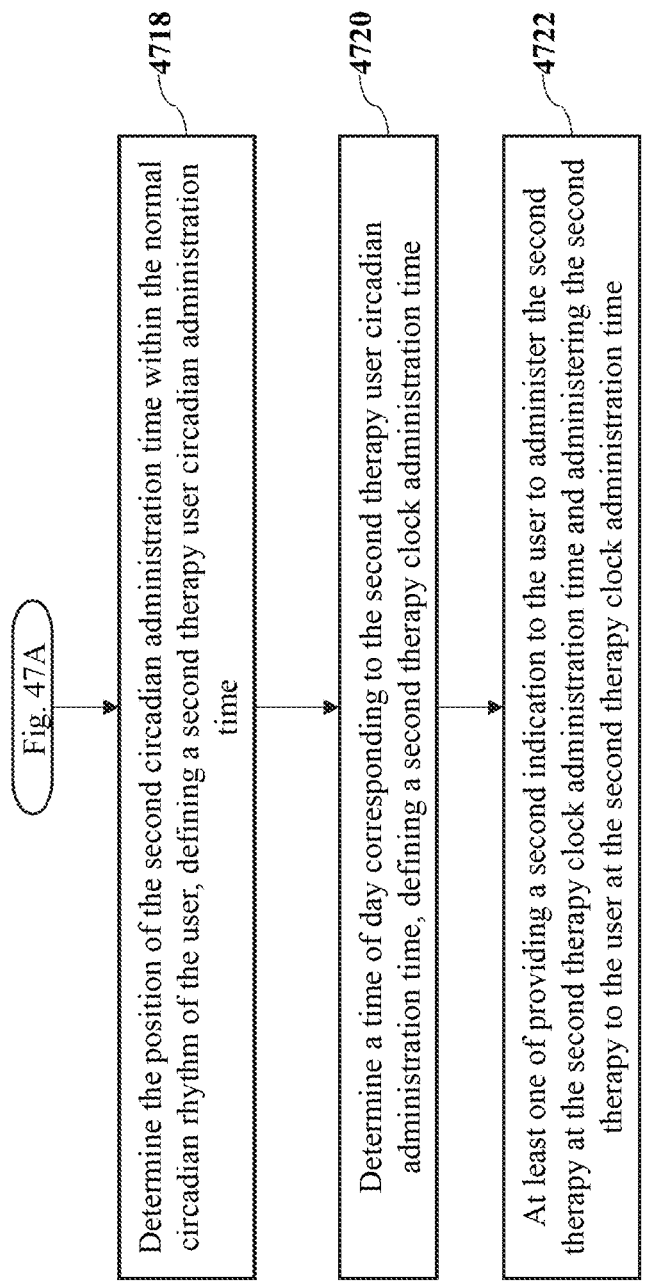

Referring now to FIGS. 47A-B, a method 4700 according to another embodiment of the invention is presented. The method 4700 may include receiving an indication of a first therapy to be administered at 4702, identifying one or more periods during a circadian cycle during which administration of the first therapy is preferred, defining a first circadian administration time, at 4704, and receiving an indication of a normal circadian rhythm of the user at 4706. The method 4700 may further continue at 4708 with determining the position of the first circadian administration time within the normal circadian rhythm of the user, defining a first user circadian administration time, at 4710 with determining a time of day corresponding to the user circadian administration time, defining a first clock administration time, and at 4712 with at least one of providing a first indication to the user to administer the first therapy at the first clock administration time and administering the first therapy to the user at the first clock administration time.

The method 4700 may further continue at 4714 with receiving a second therapy to be administered. The second therapy may be completely distinct from the first therapy, e.g. is prescribed as a result of a separate diagnosis, or it may be related to the first therapy, e.g. the first and second therapies are prescribed together as a treatment regimen. This embodiment may be distinguished from the method 4500 of FIGS. 45A-B where a second administration of the same treatment (in this embodiment, the first treatment) is administered. The method 4700 may continue at 4716 with identifying one or more periods during the circadian cycle during which administration of the second therapy is preferred, defining a second therapy circadian administration time. In the present embodiment, this identification may be made responsive to that the first therapy is also being administered. In this way, any interaction or interference arising from administration of the first therapy may be accounted for and minimized, maximized, or avoided depending on the desired effect of the interaction. In some embodiments, the second therapy circadian administration time may be determined without consideration of the administration of the first therapy. In some embodiments, where a contraindication/effect of the first therapy is sufficiently great that it may substantially negatively effect the efficacy of the second therapy at the preferred and/or any point in the circadian rhythm, a warning may be provided to the user by an auditory or visual means as described for providing an indication to the user as described above.

The method 4700 may continue at 4718 with determining the position of the second administration time within the normal circadian rhythm of the user, defining a second therapy user circadian administration time, at 4720 with determining a time of day corresponding to the second therapy user circadian administration time, defining a second therapy clock administration time, and at 4722 with at least one of providing a second indication to the user to administer the second therapy at the second therapy clock administration time and administering the second therapy to the user at the second therapy clock administration time. The second indication may be of the same or similar type of indication as the first indication or it may be completely different. In some embodiments, the second indication may be distinguishable from the first indication so that an observer, such as the user, may perceive the first indication and understand it is related to the administration of the first therapy and the second indication and understand it is related to the administration of the second therapy. For example, a first lighting device configured to emit light within a first wavelength range that is perceived by an observer as a first color may indicate the first therapy and a second lighting device configured to emit light within a second wavelength range that is perceived by an observer as a second color may indicate the second therapy.

Additionally, administration of the first and second therapies may take the form of alternatives of the methods of administering therapy as described above. For example, a first IV pump may be operated to administer the first therapy and a second IV pump may be operated to administer the second therapy. As another example, a pill box containing a plurality of compartments may be operated to open a first compartment thereof to permit access to a first medication associated with the first therapy and further operated to open a second compartment thereof to permit access to a second medication associated with the second therapy. As another example, an IV pump may be operated to administer the first therapy and a pill box may be operated to open a container thereof to facilitate access to a medication associated with the second therapy. In this way, operation of any number of devices to administer or facilitate administration of the first and second therapies is contemplated and included within the scope of the invention.

Furthermore, it is contemplated that an indication of the first clock administration time may be provided and operation of a device to administer or facilitate administration of the second therapy within the method, and vice-versa, i.e. operating a device to administer or facilitate administration of the first therapy and providing an indication of the second clock administration time.

While two therapies are disclosed, it is contemplated that the method 4700 may include any number of therapies, and each subsequent therapy may be identified, and a clock administration time determined therefore, responsive or not responsive to the clock administration times of the preceding therapies.

FIGS. 43-47 depict methods with varying functionality. It is contemplated and included within the scope of the invention that any of the functions that differ between the embodiments depicted in those figures may be selectively combined in all possible permutations, such that a method may include any and all elements of the methods shown in FIGS. 43-47 and their attending description. All permutations of such combinations are contemplated and included within the scope of the invention.

Figure 48:
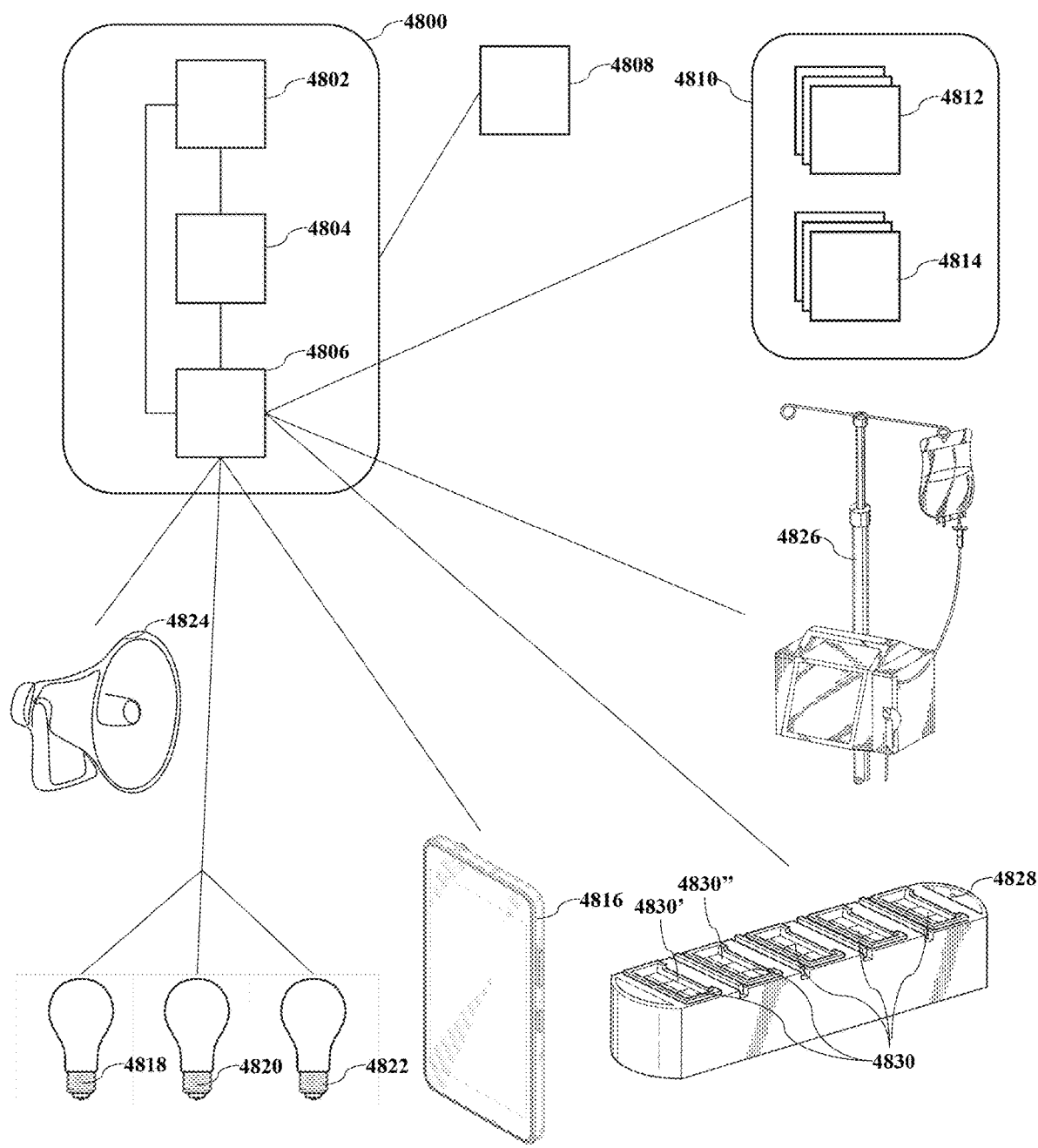
FIG. 48 is a schematic view of a system and connected devices according to an embodiment of the invention.

Referring now to FIG. 48, a system 4800 capable of performing the above-described methods is presented. The system 4800 may be a computerized device operable to receiving the indications of the treatment, the user's normal circadian rhythm, and indications of the user's present position in their circadian rhythm, as well as indications about upcoming changes to the circadian rhythm, as described above. The system 4800 may include a processor 4802. The processor 4802 may be any type of processing device as is known in the art, including, but not limited to, microprocessors. Integrated circuits (ICs), field-programmable gate arrays (FPGAs), and the like. The system 4800 may further comprise a memory device 4804. The memory device 4804 may be in communication with the processor 4802 and operable to store data and software thereon. The memory device 4804 may be a non-transitory storage medium. The memory device 4804 may be any type of storage device as is known in the art, including, but not limited to, a hard disk or other physical storage medium, a solid state drive (SSD) or any other device that uses flash memory or other electronic non-volatile computer memory storage medium, and all other storage medium devices, including non-volatile storage mediums. The system 4800 may further comprise a communication device 4806 positioned in communication with one or both of the processor 4802 and the memory device 4804. The communication device 4806 may be configured to send and receive data to remote computerized devices using any communication medium, including wired and wireless (such as radio and light-based), and communication protocol as is known in the art, including, but not limited to, Ethernet, Universal Serial Bus (USB), 802.XX protocols including Wi-Fi, Bluetooth, Zigbee, Z-Wave, LiFi, cellular communication including CDMA, TDMA, 3G, 4G, and 5G, as well as messaging protocols such as SMS, MMS, and RCS. Moreover, the network communication device may be operable to communicate any type of wide area network (WAN) as is known in the art, including the Internet and cellular communication networks, local area network (LAN) such as an Ethernet or WiFi network, and personal area network (PAN) such as a Bluetooth network. Furthermore, the system 4800 may comprise a plurality of communication devices 4806 to facilitate communication across one or more of these mediums and/or protocols. Additionally, the system 4800 may comprise software to facilitate communication across one or more of these mediums utilizing third-party services, e.g. sending an SMS message utilizing third-party services across the Internet.

In some embodiments, the system 4800 may further comprise a user input device 4808. The user input device 4808 may be any device capable of receiving an input from a user, including, but not limited to, a mouse, a keyboard, a touchscreen, a microphone, a camera, pushbuttons, switches, toggles, trackpads, and the like.

The system 4800 may be positioned in communication with one or more remote computerized devices, specifically a server 4810 that comprises one or more database 4812, 4814 the contain information regarding therapies and their relationship to circadian rhythms as described above. It is contemplated and included within the scope of the invention that the system 4800 may communicate with multiple servers or other devices that comprises databases to obtain all necessary information for performing the above-described methods.

Additionally, the system 4800 may be positioned in communication with one or more indicating devices. Types of indicating devices include remote computerized devices, such as a smartphone 4816, one or more light-emitting devices 4818, 4820, 4822, and an audio device 4824 such as a speaker. The system 4800 may communicate with these devices utilizing the network communication device 4806 or other computer hardware as is known in the art, including an audio output device, such as a sound card. The system 600 may send messages to the smartphone 4816 by any means or method as is known in the art, including push notifications to software running on the smartphone 616, SMS, MMS, or RCS messages, or placing an automated telephone call that the user may receive and hear an automated announcement regarding administering a therapy. Additionally, as described above, the system may generate either a tonal indication, a spoken indication, or other audible indication using the speaker 4824. Furthermore, the system 4800 may control the operation of one or more of the light-emitting devices 4818, 4820, 4822 to indicate administration of a therapy. As suggested above, the light emitting devices 4818, 4820, 4822 may each be configured to emit light within a different wavelength range that is perceived by an observer as different colors, and those colors may be associated with different therapies, and the system may selectively illuminate one or more to indicate the different therapies are to be administered. In some embodiments, a lighting device may be operable to selectively emit light within different wavelength ranges perceived as different colors, the different colors being associated with different therapies, and the system may be configured to selectively illuminate the lighting device to emit the different colors in indicate the therapies to be administered.

Additionally, the system 4800 may be configured to operate one or more devices configured to administer therapies or facilitate the administration of therapies. For example, the system 4800 may be positioned in operative communication with an IV pump 4826 operable to dispense medication into a patient. The system 4800 may be configured to operate the IV pump 4826 to administer a therapy as described above. As another example, the system 4800 may be positioned in operative communication with a pill box 4828. The pill box 4828 may comprise a plurality of lidded compartments 4830 that may be operated by the system 4800 to selectively open. The system 4800 may be configured to selectively operate the pill box 4828 to open a first compartment 4830' of the plurality of compartments 4830 comprising a first medication associated with a first therapy as described above, to open a second compartment 4830" of the plurality of compartments 4830 comprising a second medication associated with a second therapy as described above, etc., thereby facilitating retrieval of the medications and administration thereof. These devices are exemplary only; the system 4800 may be positioned in operative communication with any device that may administer or facilitate administration of therapy as is known in the art and configured to selectively operate the device to administer or facilitate administration therapy as described above. Moreover, the system 4800 may be positioned in communication with multiple devices of varying operation and capabilities, e.g. an IV pump 4826 and a pill box 4828 as described herein, and configured to selectively operate those devices to administer or facilitate administration of therapy. Furthermore, it is contemplated and included within the scope of the invention that one or more of the processor 4802, the communication device 4806, or other hardware as may be comprised by the system 4800 may enable it to operate the devices.

Figure 49:
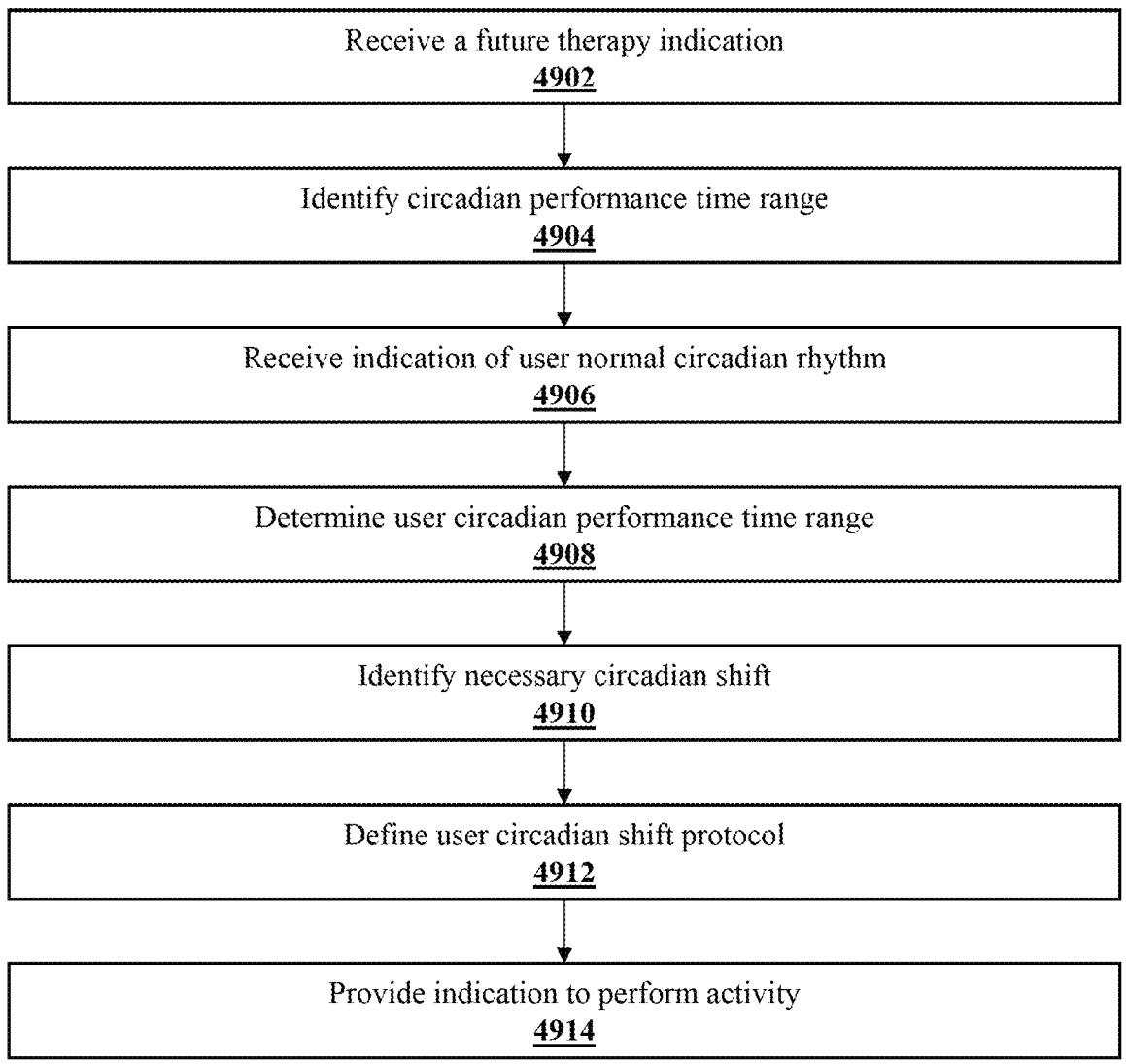
FIG. 49 is a flow chart illustrating a method according to an embodiment of the invention.

Referring now to FIG. 49, a method 4900 according to an embodiment of the invention is presented. The method 4900 may comprise receiving a future therapy indication at step 4902. The indication may comprise various types of information, including a therapy to be administered, a therapy date defining the day the therapy will be administered, and a therapy time defining a time of day the therapy will be administered. The therapy, therapy date, and therapy time may be the same as described hereinabove. The method 4900 may further comprise identifying one or more periods during a circadian cycle during which performance of the therapy is preferred, defining a circadian performance time range, at step 4904. The time range may encompass the period of the circadian rhythm during which therapy administration is most efficacious. The method 4900 may continue at step 4906 with receiving an indication of a normal circadian rhythm of the user, similar to the indication received above at 4306 of FIG. 43. The normal circadian rhythm of the user may be at least one of a central circadian clock of the user and a peripheral circadian clock of the user. The method 4900 may further continue at step 4908 with determining the position of the circadian performance time range within the normal circadian rhythm of the user, defining a user circadian performance time range. This determination will reflect any difference between the user's normal circadian rhythm and the circadian rhythm that will align with the circadian performance time range.

The method 4900 may continue at step 4910 with identifying a circadian shift necessary to change the user circadian performance time range such that the therapy time occurs within the user circadian performance time range, the circadian shift comprising a circadian shift direction and a circadian shift magnitude. For example, if the normal circadian rhythm of the user is one hour ahead of the preferred circadian rhythm, i.e. the circadian rhythm that aligns with the circadian performance time range, then a delay circadian shift of one hour will be identified. As another example, if the normal circadian rhythm of the user is two hours behind the preferred circadian rhythm, then an advance shift of two hours will be identified.

The method 4900 may continue at 4912 with defining a user circadian shift protocol responsive to the circadian shift direction, circadian shift magnitude, and a number of days between a present day and the therapy date, the user circadian shift protocol comprising one or more activities scheduled to be performed at a certain date and time. The user circadian shift protocol may be a series of activities to be performed at certain times to effectuate a circadian advance or delay as described above, including at least those activities described for method 100 above. In some embodiments, the activities may comprise at least one of a light exposure or light avoidance activity, a chronobiotic activity, a nutritional consumption activity, a physical activity, and a rest activity.

The method 4900 may continue at 4914 with providing an indication to perform an activity of the one or more activities comprised by the user circadian shift protocol. The indication may be provided by a variety of means and methods as described above, namely, illuminating an indicator light, operating a sound-generating device to provide an audio indication, operating a visual display to display a message, and transmitting a message to be received on a computerized device.

In some embodiments, the user circadian shift protocol may be determined responsive to receiving one or more user inputs, such as receiving a sleep pattern for the user, receiving excluded activities for the user, and receiving preferred activities for the user.

In some embodiments, the method 4900 may further comprise receiving an indication of non-performance of an activity, defining a non-performed activity (not shown). In such embodiments, the user circadian shift protocol may be adjusted responsive to the non-performed activity.

Figure 50:
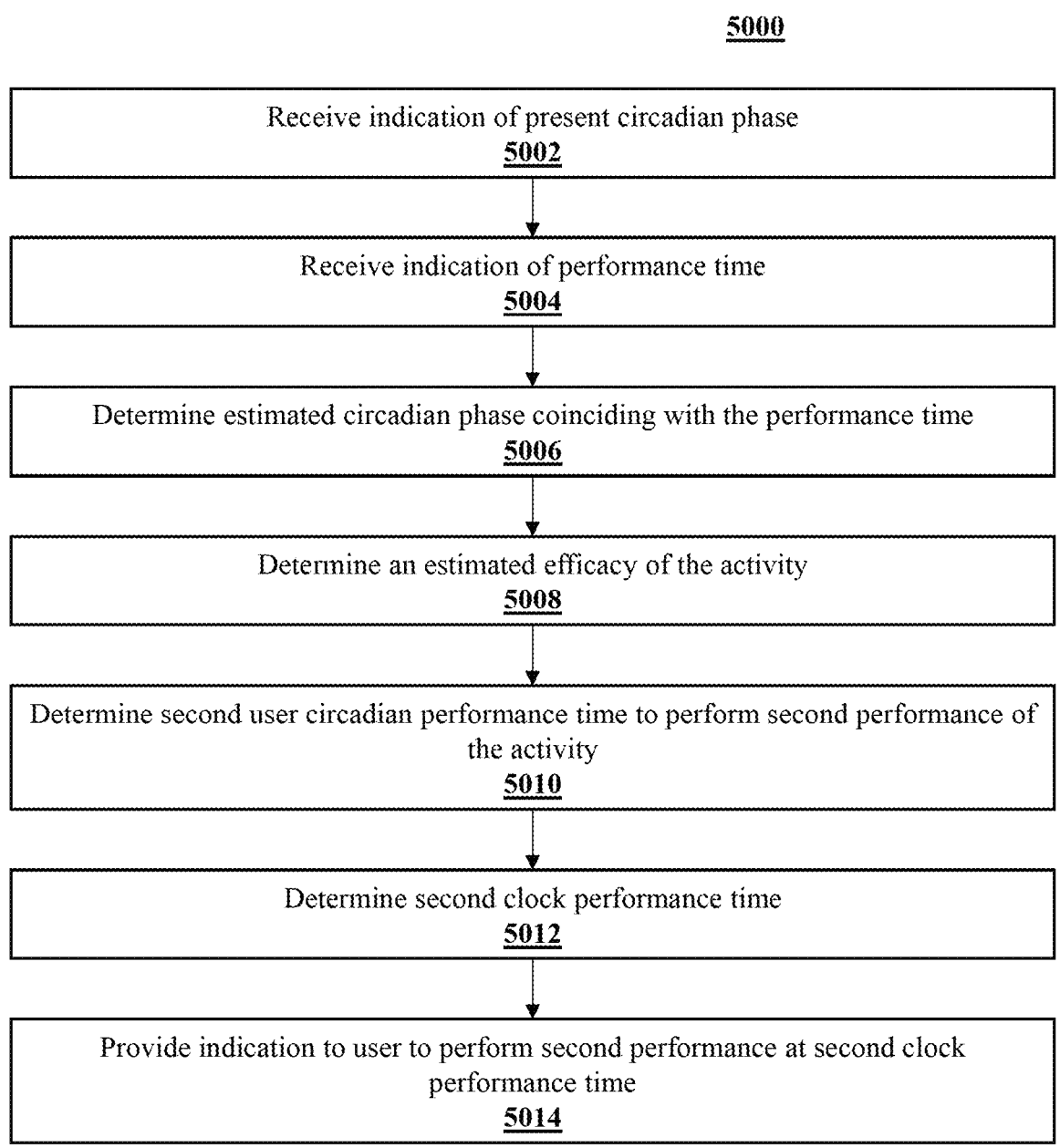
FIG. 50 is a flow chart illustrating a further embodiment of the method of FIG. 49.

Referring now to FIG. 50, a method 5000 showing supplemental aspects of method 4900 is presented. It is contemplated that, in some embodiments, defining a user circadian shift protocol may comprise determining a time of day corresponding to the user circadian performance time, defining a clock performance time. Additionally, in further embodiments, providing an indication to perform the activity comprises providing the indication at the clock performance time. The method 5000 may comprise receiving an indication of a present circadian phase of the user at step 5002. This indication may be any type of indication of the present circadian phase of the user, as described above. Additionally, in some embodiments, the indication of the present circadian phase of the user may be used in determining the clock performance time.

The method 5000 may continue at step 5004 with receiving an indication of when the activity was performed, defining a performance time, and at step 5006 with determining an estimated circadian phase coinciding with the performance time. The estimated circadian phase may be determined based on at least one of the indication of the present circadian phase and the normal circadian phase of the user. The method 5000 may continue at 5008 with determining an estimated efficacy of the activity responsive to the estimated circadian phase, where the estimated efficacy is less than an ideal efficacy. Similar to therapies having varying efficacy based on what circadian phase the therapy is administered, performing one of the various activities identified above may have varying efficacy in terms of effectuating a circadian shift depending on the circadian phase the user was in when the activity was performed. In some embodiments, he circadian shift protocol may be designed based on the assumption that the activities performed will have a maximum or ideal efficacy. Performing the activities outside of the circadian phase during which the activity will have an ideal efficacy may result in the previously-determined protocol not effectuating a circadian shift of the desired magnitude, resulting in the therapy being less than desirably efficacious. Accordingly, where the estimated efficacy is less than the ideal efficacy, the method 5000 may further comprise determining a second user circadian performance time to perform a second performance of the activity responsive to at least one of the estimated efficacy, the circadian performance time, the user circadian performance time, and a second indication of the present circadian phase of the user at step 5010, the second user circadian performance time being a period during the circadian rhythm of the user that performance of the second activity will have a desired efficacy, in some instances an ideal efficacy. The second performance of the activity may be the same activity as was performed previously by the user and may result in effectuating another circadian shift to compensate for the reduced efficacy of the circadian shift accomplished by the first performance of the activity.

The method 5000 may continue at step 5012 with determining a second clock performance time responsive to the second user circadian performance time, the second clock performance time being the time of day the user is intended to perform the second performance of the activity. The method 5000 may conclude at step 5014 with providing an indication to the user to perform the second performance of the activity at the second clock performance time, the indication being either the same as or a different type of indication as the indication for the first performance of the activity.

Figure 51:
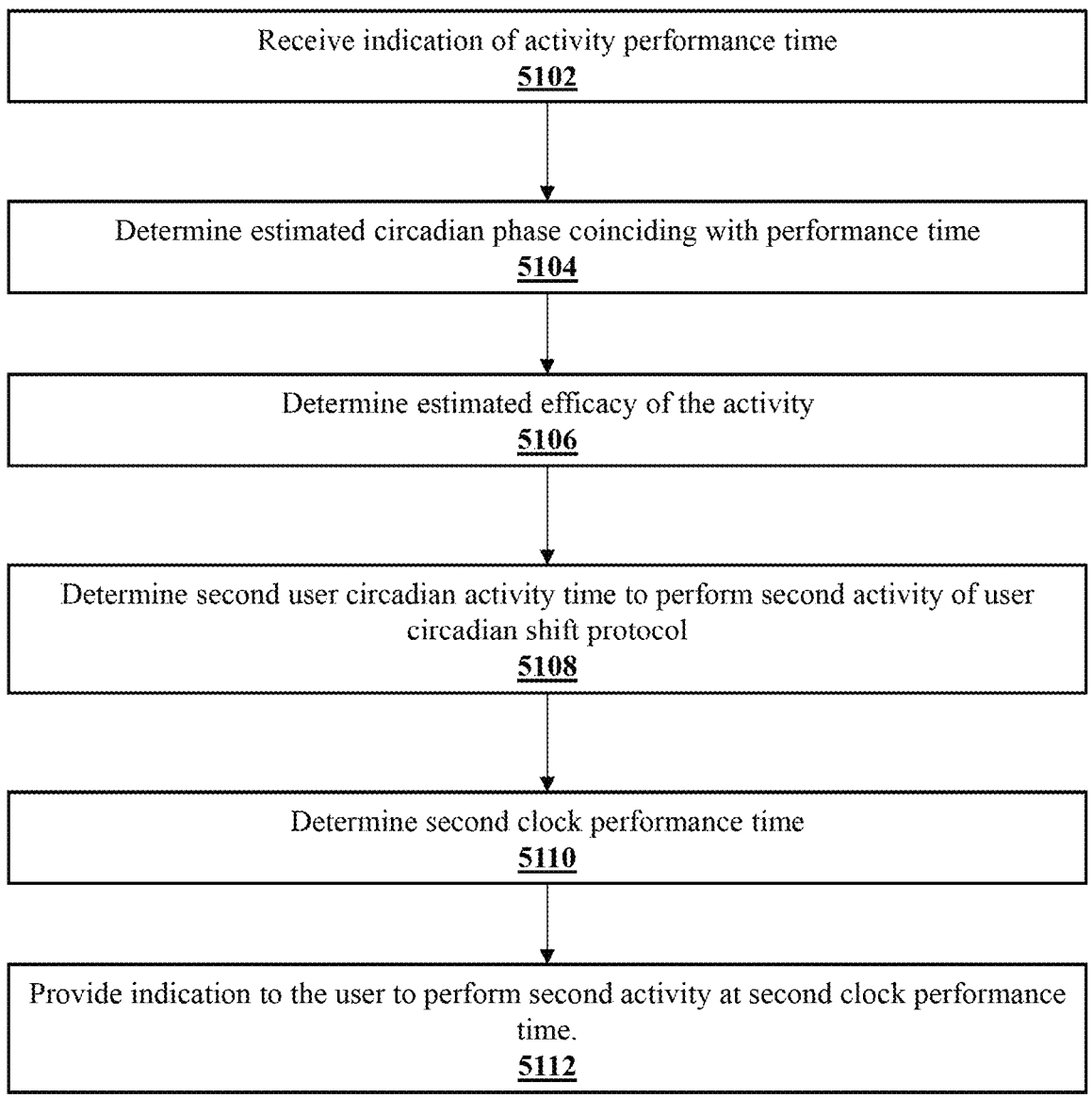
FIG. 51 is a flow chart illustrating a further embodiment of the method of FIG. 49.

In other embodiments, the second activity may be a different activity from the first activity. Referring now to FIG. 51, a method 5100 according to such an embodiments is presented. The method 5100 may begin at step 5102 with receiving an indication of when the activity was performed, defining a performance time. The method 5100 may continue at step 5104 with determining an estimated circadian phase coinciding with the performance time, at step 5106 with determining an estimated efficacy of the activity responsive to the estimated circadian phase, where the estimated efficacy is less than an ideal efficacy, and at step 5108 with determining a second user circadian activity time to perform a second activity of the user circadian shift protocol responsive to at least one of the estimated efficacy, the circadian performance time, and the user circadian performance time. The second activity is different from the first activity. The method 5100 may continue at step 5110 with determining a second clock performance time responsive to the second user circadian activity time and conclude at step 5112 with providing an indication to the user to perform the second activity at the second clock performance time.

Figure 52:
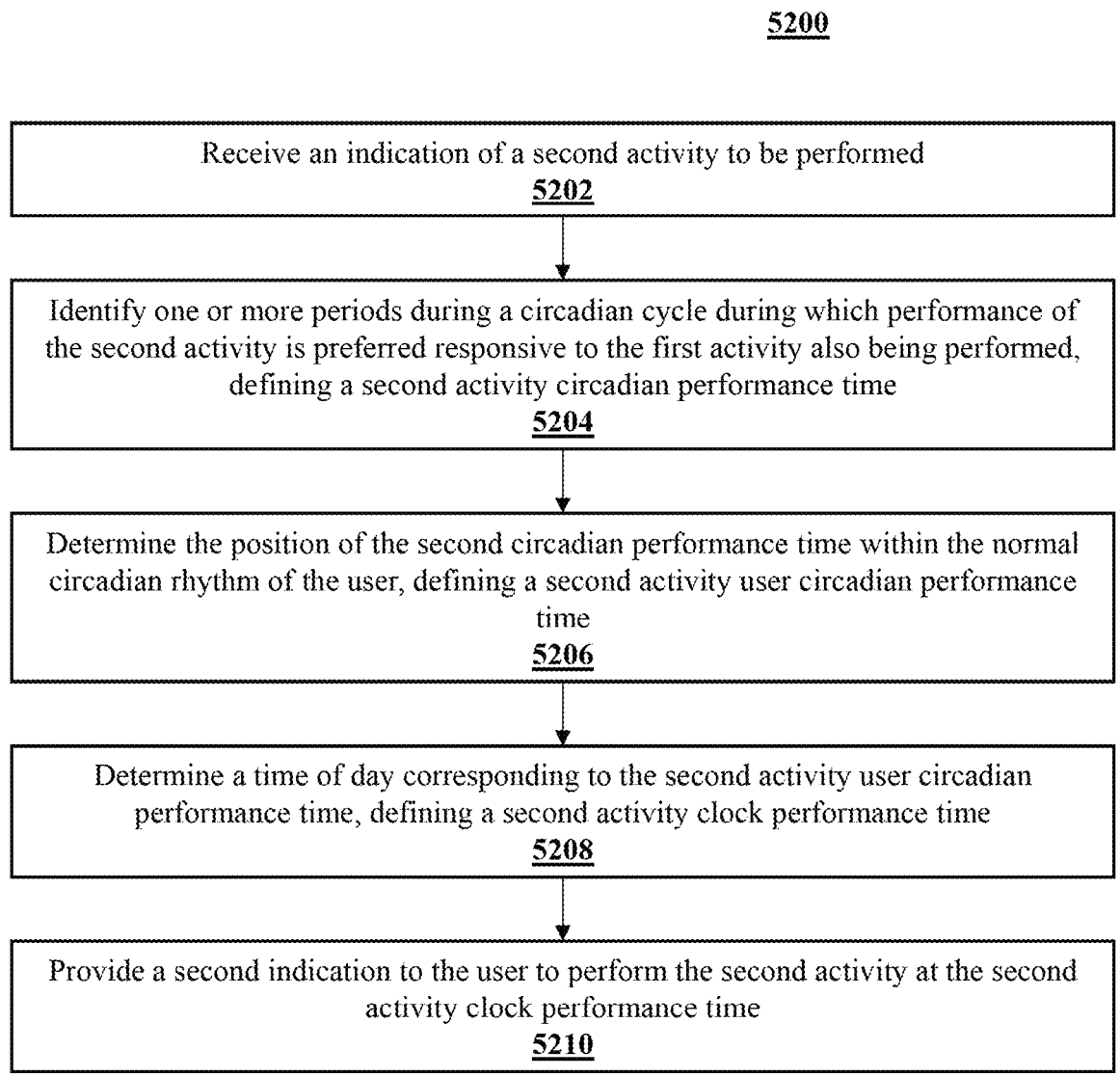
FIG. 52 is a flow chart illustrating a further embodiment of the method of FIG. 49.

A further embodiment comprising a second activity is presented as method 5200 in FIG. 52. In this embodiment, the circadian performance time is a first therapy circadian performance time, the user circadian performance time is a first activity user circadian performance time, the clock performance time is a first activity clock performance time, and the indication provided to the user to perform the activity is a first indication. The method 5200 may start at step 5202 with receiving an indication of a second activity to be performed. The method 5200 may continue at step 5204 with identifying one or more periods during a circadian cycle during which performance of the second activity is preferred responsive to the first activity also being performed, defining a second activity circadian performance time, at step 5206 with determining the position of the second circadian performance time within the normal circadian rhythm of the user, defining a second activity user circadian performance time, and at step 5208 determining a time of day corresponding to the second activity user circadian performance time, defining a second activity clock performance time. The method 5200 may conclude at step 5210 with providing a second indication to the user to perform the second activity at the second activity clock performance time. In this embodiment, the first activity circadian performance time may be determined responsive to the second activity also being performed. In some such embodiments, providing the first indication to the user to perform the first activity comprises at least one of illuminating a first indicator light, operating a sound-generating device to provide a first audio indication, operating a visual display to display a first message, and transmitting a first message to be received on a computerized device, and providing the second indication to the user to perform the second activity comprises at least one of illuminating a second indicator light that is differentiated from the first indicator light, operating a sound-generating device to provide a second audio indication that is differentiated from the first audio indication, operating a visual display to display a second message that is differentiated from the first message, and transmitting a second message that is differentiated from the first message to be received on the computerized device.

Some of the illustrative aspects of the present invention may be advantageous in solving the problems herein described and other problems not discussed which are discoverable by a skilled artisan.

While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

Thus the scope of the invention should be determined by the appended claims and their legal equivalents, and not by the examples given.

The claims in the instant application are different than those of the parent application or other related applications. Applicant therefore rescinds any disclaimer of claim scope made in the parent application or any predecessor application in relation to the instant application. Any such previous disclaimer and the cited references that it was made to avoid, may need to be revisited. Further, any disclaimer made in the instant application should not be read into or against the parent application.

What is claimed is:

1. A method of determining and facilitating shifting of a circadian rhythm of a user to improve the effectiveness of a future therapy by a server comprising a processor, the method comprising:
receiving at the server a future therapy indication comprising:
a therapy to be administered;
a therapy date defining the day the therapy will be administered; and
a therapy time defining a time of day the therapy will be administered;
identifying by the processor one or more periods during a circadian cycle during which performance of the therapy is preferred, defining a circadian performance time range;
receiving at the server an indication of a normal circadian rhythm of the user;
determining by the processor the position of the circadian performance time range within the normal circadian rhythm of the user, defining a user circadian performance time range;
identifying by the processor a circadian shift necessary to change the user circadian performance time range such that the therapy time occurs within the user circadian performance time range, the circadian shift comprising a circadian shift direction and a circadian shift magnitude;
receiving at the server an indication of a present circadian phase of the user;
defining by the processor a user circadian shift protocol responsive to the circadian shift direction, circadian shift magnitude, and a number of days between a present day and the therapy date, the user circadian shift protocol comprising one or more activities scheduled to be performed at a certain date and time and comprising:
receiving at the server an indication of a second activity to be performed and comprised by the one or more activities;
determining by the processor a first time of day to perform a first activity of the one or more activities corresponding to the user circadian performance time range responsive to the present circadian phase of the user and the second activity, defining a first activity clock performance time;
identifying by the processor one or more periods during a circadian cycle during which performance of the second activity is preferred responsive to the first activity, defining a second activity circadian performance time;
determining by the processor the position of the second circadian performance time within the normal circadian rhythm of the user, defining a second activity user circadian performance time; and
determining by the processor a second time of day corresponding to the second activity user circadian performance time, defining a second activity clock performance time;
providing by the processor a first indication to perform the first activity of the one or more activities comprised by the user circadian shift protocol at the first activity clock performance time comprising at least one of illuminating a first indicator light, operating a sound-generating device to provide a first audio indication, operating a visual display to display a first message, and transmitting a first message to be received on a computerized device; and;

providing by the processor a second indication to the user to perform the second activity at the second activity clock performance comprising at least one of illuminating a second indicator light that is differentiated from the first indicator light, operating a sound-generating device to provide a second audio indication that is differentiated from the first audio indication, operating a visual display to display a second message that is differentiated from the first message, and transmitting a second message that is differentiated from the first message to be received on the computerized device.

2. The method of claim 1 wherein the one or more activities comprises at least one of a light exposure or light avoidance activity, a chronobiotic activity, a nutritional consumption activity, a physical activity, and a rest activity.

3. The method of claim 1 wherein providing an indication to perform the activity comprises at least one of illuminating an indicator light, operating a sound-generating device to provide an audio indication, operating a visual display to display a message, and transmitting a message to be received on a computerized device.

4. The method of claim 1 wherein the normal circadian rhythm of the user is at least one of a central circadian clock of the user and a peripheral circadian clock of the user.

5. The method of claim 1 wherein the present circadian phase is a first present circadian phase, the method further comprising:
receiving at the server an indication of when the activity was performed, defining a performance time;
determining by the processor an estimated circadian phase coinciding with the performance time;
determining by the processor an estimated efficacy of the activity responsive to the estimated circadian phase, where the estimated efficacy is less than an ideal efficacy;
determining by the processor a second user circadian performance time to perform a second performance of the activity responsive to at least one of the estimated efficacy, the circadian performance time, the user circadian performance time, and a second indication of the present circadian phase of the user;
determining by the processor a second clock performance time responsive to the second user circadian performance time; and
providing by the server an indication to the user to perform the second performance of the activity at the second clock performance time.

6. The method of claim 1 wherein the indication of the present circadian phase of the user and the normal circadian rhythm of the user is at least one of a sleep-wake cycle of the user, light-dark exposure, chronotype, sex, age, present time zone, future time zone, present work shift, future work shift, heat rate, heart rate variability, core temperature, skin temperature, and a biological marker.

7. The method of claim 1 further comprising:
receiving at the server an indication of when the activity was performed, defining a performance time;
determining by the processor an estimated circadian phase coinciding with the performance time;
determining by the processor an estimated efficacy of the activity responsive to the estimated circadian phase, where the estimated efficacy is less than an ideal efficacy;
determining by the processor a second user circadian activity time to perform a second activity of the user circadian shift protocol responsive to at least one of the estimated efficacy, the circadian performance time, and the user circadian performance time;
determining by the processor a second clock performance time responsive to the second user circadian activity time; and
providing by the processor an indication to the user to perform the second activity at the second clock performance time.

8. The method of claim 1 further comprising receiving at the server an indication of a present circadian phase of the user; wherein each of the first activity clock performance time and the second activity clock performance time is determined responsive to the present circadian phase of the user.

9. The method of claim 1 further comprising receiving at the server a sleep pattern for the user, wherein the user circadian shift protocol is defined responsive to the sleep pattern.

10. The method of claim 1 further comprising receiving at the server an activity preference indication for the user identifying an activity the user will not perform, defining an excluded activity; wherein defining the user circadian shift protocol comprises defining one or more activities excluding the excluded activity.

11. The method of claim 1 further comprising:
receiving at the server an indication of non-performance of an activity, defining a non-performed activity; and
adjusting the user circadian shift protocol responsive to the non-performed activity.

12. A method of determining and facilitating shifting of a circadian rhythm of a user to improve the effectiveness of a future therapy by a server comprising a processor, the method comprising:
receiving at the server a future therapy indication comprising:
a therapy to be administered;
a therapy date defining the day the therapy will be administered; and
a therapy time defining a time of day the therapy will be administered;
identifying by the processor one or more periods during a circadian cycle during which performance of the therapy is preferred, defining a circadian performance time range;
receiving at the server an indication of a normal circadian rhythm of the user;
receiving at the server an indication of a present circadian phase of the user;
determining by the processor the position of the circadian performance time range within the normal circadian rhythm of the user, defining a user circadian performance time range;
identifying by the processor a circadian shift necessary to change the user circadian performance time range such that the therapy time occurs within the user circadian performance time range, the circadian shift comprising a circadian shift direction and a circadian shift magnitude;
defining by the processor a user circadian shift protocol responsive to the circadian shift direction, circadian shift magnitude, and a number of days between a present day and the therapy date, the user circadian shift protocol comprising one or more activities scheduled to be performed at a date and time of day corresponding to the user circadian performance time, defining a clock performance time, comprising:

receiving at the server an indication of a second activity to be performed and comprised by the one or more activities;

determining by the processor a first time of day to perform a first activity of the one or more activities corresponding to the user circadian performance time range responsive to the present circadian phase of the user and the second activity, defining a first activity clock performance time;

identifying by the processor one or more periods during a circadian cycle during which performance of the second activity is preferred responsive to the first activity, defining a second activity circadian performance time;

determining by the processor the position of the second circadian performance time within the normal circadian rhythm of the user, defining a second activity user circadian performance time; and determining by the processor a second time of day corresponding to the second activity user circadian performance time, defining a second activity clock performance time;

providing by the server an indication to perform an activity of the one or more activities at the clock performance time at the first activity clock performance time comprising at least one of illuminating a first indicator light, operating a sound-generating device to provide a first audio indication, operating a visual display to display a first message, and transmitting a first message to be received on a computerized device; and providing by the processor a second indication to the user to perform the second activity at the second activity clock performance comprising at least one of illuminating a second indicator light that is differentiated from the first indicator light, operating a sound-generating device to provide a second audio indication that is differentiated from the first audio indication, operating a visual display to display a second message that is differentiated from the first message, and transmitting a second message that is differentiated from the first message to be received on the computerized device;

wherein the one or more activities comprises at least one of a light exposure or light avoidance activity, a chronobiotic activity, a nutritional consumption activity, a physical activity, and a rest activity.

13. The method of claim 12 wherein the present circadian phase is a first present circadian phase, the method further comprising:

receiving at the server an indication of when the activity was performed, defining a performance time;

determining by the processor an estimated circadian phase coinciding with the performance time;

determining by the processor an estimated efficacy of the activity responsive to the estimated circadian phase, where the estimated efficacy is less than an ideal efficacy;

determining by the processor a second user circadian performance time to perform a second performance of the activity responsive to at least one of the estimated efficacy, the circadian performance time, the user circadian performance time, and a second indication of the present circadian phase of the user;

determining by the processor a second clock performance time responsive to the second user circadian performance time; and providing by the server an indication to the user to perform the second performance of the activity at the second clock performance time.

14. The method of claim 12 wherein the indication of the present circadian phase of the user and the normal circadian rhythm of the user is at least one of a sleep-wake cycle of the user, light-dark exposure, chronotype, sex, age, present time zone, future time zone, present work shift, future work shift, heat rate, heart rate variability, core temperature, skin temperature, and a biological marker.

15. The method of claim 12 further comprising:

receiving at the server an indication of when the activity was performed, defining a performance time;

determining by the processor an estimated circadian phase coinciding with the performance time;

determining by the processor an estimated efficacy of the activity responsive to the estimated circadian phase, where the estimated efficacy is less than an ideal efficacy;

determining by the processor a second user circadian activity time to perform a second activity of the therapy responsive to at least one of the estimated efficacy, the circadian performance time, and the user circadian performance time;

determining by the processor a second clock performance time responsive to the second user circadian activity time responsive to the second user circadian activity time; and at least one of providing by the server an indication to the user to perform the second performance of the activity at the second clock performance time and administering the second performance of the therapy to the user at the second clock performance time.

16. The method of claim 12 further comprising receiving at the server an indication of a present circadian phase of the user; wherein each of the first clock performance time and the second clock performance time is determined responsive to the present circadian phase of the user.

17. A system for determining and facilitating shifting of a circadian rhythm of a user to improve the effectiveness of a future therapy comprising:

a communication device configured to:
  receive a future therapy indication comprising:
    a therapy to be administered;
    a therapy date defining the day the therapy will be administered; and
    a therapy time defining a time of day the therapy will be administered;
  receive an indication of a normal circadian rhythm of the user;
  receive an indication of a present circadian phase of the user;
  receive an indication of a second activity to be performed; and
  transmit a message to be received on a computerized device;

a processor positioned in communication with the communication device and configured to:
  identify one or more periods during a circadian cycle during which performance of the therapy is preferred, defining a circadian performance time range;

determine the position of the circadian performance time range within the normal circadian rhythm of the user, defining a user circadian performance time range;

define a user circadian shift protocol responsive to the circadian shift direction, circadian shift magnitude, and a number of days between a present day and the therapy date, the user circadian shift protocol comprising one or more activities scheduled to be performed at a certain date and time, comprising:

determining a first time of day to perform a first activity of the one or more activities corresponding to the user circadian performance time range responsive to the present circadian phase of the user and the second activity, defining a first activity clock performance time;

identifying one or more periods during a circadian cycle during which performance of the second activity is preferred responsive to the first activity, defining a second activity circadian performance time;

determining by the processor the position of the second circadian performance time within the normal circadian rhythm of the user, defining a second activity user circadian performance time; and determining by the processor a second time of day corresponding to the second activity user circadian performance time, defining a second activity clock performance time;

at least one of illuminate an indicator light, operate a sound-generating device to provide an audio indication, and operate a visual display to display a message at the first clock performance time; and at least one of illuminate an indicator light, operate a sound-generating device to provide an audio indication, and operate a visual display to display a message at the second clock performance time.

18. The system of claim 17 wherein:

the present circadian phase is a first present circadian phase;

the communication device is further configured to receive an indication of when the activity was performed, defining a performance time;

the processor is further configured to:

determine an estimated circadian phase coinciding with the performance time;

determine an estimated efficacy of the activity responsive to the estimated circadian phase, where the estimated efficacy is less than an ideal efficacy;

determine a second user circadian performance time to perform a second performance of the activity responsive to at least one of the estimated efficacy, the circadian performance time, the user circadian performance time, and a second indication of the present circadian phase of the user;

determine a second clock performance time responsive to the second user circadian performance time; and at least one of illuminate an indicator light, operate a sound-generating device to provide an audio indication, and operate a visual display to display a message at the second clock performance time; and wherein the communication device is further configured to transmit the message to be received on a user computerized device at the second clock performance time.

19. The system of claim 17 wherein the communication device is configured to transmit the message to be received on a user computerized device by at least one of transmitting the message directly to the computerized device and transmitting the message to the computerized device across a network according to a network protocol.

* * * * *